(12) United States Patent
Peterson et al.

(10) Patent No.: US 9,713,629 B2
(45) Date of Patent: Jul. 25, 2017

(54) COMPOSITIONS AND METHODS FOR TREATING AND PREVENTING TISSUE INJURY AND DISEASE

(71) Applicant: MICROVASCULAR TISSUES, INC., Beverly, MA (US)

(72) Inventors: Dale R. Peterson, Carlsbad, CA (US); Ralph-Heiko Mattern, Ramona, CA (US); Corey Wilson-Wirth, San Diego, CA (US); Kevin L. Ohashi, Jamaica Plain, MA (US)

(73) Assignee: MicroVascular Tissues, Inc., Beverly, MA (US)

( * ) Notice: Subject to any disclaimer, the term of this patent is extended or adjusted under 35 U.S.C. 154(b) by 25 days.

(21) Appl. No.: 14/429,511

(22) PCT Filed: Sep. 17, 2013

(86) PCT No.: PCT/US2013/060181
§ 371 (c)(1),
(2) Date: Mar. 19, 2015

(87) PCT Pub. No.: WO2014/047067
PCT Pub. Date: Mar. 27, 2014

(65) Prior Publication Data
US 2015/0231183 A1 Aug. 20, 2015

Related U.S. Application Data

(60) Provisional application No. 61/703,203, filed on Sep. 19, 2012.

(51) Int. Cl.
*A61K 35/44* (2015.01)
*A61L 27/36* (2006.01)
*A61L 27/54* (2006.01)
*A61L 27/38* (2006.01)
*A61K 35/12* (2015.01)

(52) U.S. Cl.
CPC .......... *A61K 35/44* (2013.01); *A61K 35/12* (2013.01); *A61L 27/3625* (2013.01); *A61L 27/3687* (2013.01); *A61L 27/3691* (2013.01); *A61L 27/3834* (2013.01); *A61L 27/54* (2013.01); *A61L 2300/41* (2013.01); *A61L 2300/412* (2013.01); *A61L 2430/10* (2013.01); *A61L 2430/34* (2013.01)

(58) Field of Classification Search
None
See application file for complete search history.

(56) References Cited

U.S. PATENT DOCUMENTS

| | | |
|---|---|---|
| 5,358,931 A | 10/1994 | Rubinsky et al. |
| 5,656,498 A | 8/1997 | Iijima et al. |
| 5,786,207 A | 7/1998 | Katz et al. |
| 6,200,606 B1 | 3/2001 | Peterson et al. |
| 7,270,946 B2 | 9/2007 | Brockbank et al. |
| 7,560,276 B2 | 7/2009 | Harmon et al. |
| 7,659,111 B2 | 2/2010 | Meir et al. |
| 8,048,671 B2 * | 11/2011 | Hendriks ............ A61L 27/3817 435/373 |
| 8,119,398 B2 | 2/2012 | Sayre et al. |
| 9,044,430 B2 | 6/2015 | Peterson et al. |
| 2006/0147430 A1 | 7/2006 | Sayre et al. |
| 2007/0274960 A1 | 11/2007 | Harman et al. |
| 2007/0292401 A1 | 12/2007 | Harmon et al. |
| 2008/0033572 A1 | 2/2008 | D'Antonio et al. |
| 2009/0324558 A1 | 12/2009 | Attawia et al. |
| 2010/0068245 A1 | 3/2010 | Manders |
| 2010/0124563 A1 | 5/2010 | Coleman et al. |
| 2012/0164113 A1 | 6/2012 | Victor |
| 2012/0183673 A1 | 7/2012 | Arsan et al. |
| 2013/0071358 A1 | 3/2013 | Peterson et al. |
| 2014/0255357 A1 | 9/2014 | Burt |
| 2015/0218506 A1 | 8/2015 | Nash et al. |
| 2016/0015859 A1 | 1/2016 | Peterson et al. |
| 2016/0271187 A1 | 9/2016 | Peterson et al. |

FOREIGN PATENT DOCUMENTS

| | | | |
|---|---|---|---|
| CN | 101757691 A | * | 6/2010 |
| EP | 0668013 A2 | | 8/1995 |
| WO | WO 97/26326 A1 | | 7/1997 |
| WO | WO 2004/006961 A1 | | 1/2004 |
| WO | WO 2004/022078 A1 | | 3/2004 |
| WO | WO 2005/035742 A2 | | 4/2005 |
| WO | WO 2007/015252 | | 2/2007 |
| WO | WO 2008/013863 A2 | | 1/2008 |
| WO | WO 2009/115581 | | 9/2009 |
| WO | WO 2012/024573 A2 | | 2/2012 |
| WO | WO 2012/154301 A1 | | 11/2012 |
| WO | WO 2014/047067 A1 | | 3/2014 |

OTHER PUBLICATIONS

Iyer, Anti-inflammatory effects of mesenchymal stem cells: novel concept for future therapies. Expert opinion on biological therapy, (May 2008)vol. 8, No. 5, pp. 569-581.*
Office Action for U.S. Appl. No. 15/148,821, mailed Jul. 7, 2016, 11 pages.
Office Action for U.S. Appl. No. 15/148,821, mailed Sep. 8, 2016, 12 pages.
Office Action for U.S. Appl. No. 14/698,763, mailed Jul. 29, 2016, 11 pages.
European Patent Application No. EP 12782247.6, Extended European Search Report dated Sep. 17, 2014, 9 pages.
European Patent Application No. EP 13839621.3, Extended European Search Report dated Mar. 29, 2016, 8 pages.
International Application No. PCT/US2012/029568, International Search Report and Written Opinion mailed Jul. 2, 2012, 7 pages.
International Application No. PCT/US2012/029568, International Preliminary Report on Patentability mailed Sep. 24, 2013, 6 pages.
International Application No. PCT/US2013/060181, International Search Report and Written Opinion mailed Nov. 25, 2013, 22 pages.

(Continued)

*Primary Examiner* — Qiuwen Mi

(57) ABSTRACT

The present invention provides novel compositions comprising multipotent cells or microvascular tissue, wherein the cells or tissue has been sterilized and/or treated to inactivated viruses, and related methods of using these compositions to treat or prevent tissue injury or disease in an allogeneic subject.

1 Claim, 17 Drawing Sheets

(56) References Cited

OTHER PUBLICATIONS

International Application No. PCT/US2013/060181, International Preliminary Report on Patentability mailed Mar. 24, 2015, 17 pages.
U.S. Appl. No. 13/423,171, Office Action mailed Apr. 24, 2013, 7 pages.
U.S. Appl. No. 13/423,171, Office Action mailed Sep. 10, 2013, 9 pages.
U.S. Appl. No. 13/423,171, Office Action mailed Mar. 18, 2014, 5 pages.
Aslan, H. et al., "Osteogenic differentiation of noncultured immunoisolated bone marrow-derived CD105+ cells." Stem Cells, 24(7): 1728-1737 (2006).
Baer and Geiger, "Adipose-derived mesenchymal stromal/stem cells: tissue localization, characterization, and heterogeneity." Stem Cells International, Article ID 812693, 11 pages. Epub Apr. 12, 2012 (2012).
Hanson, S. E. et al., "Clinical Applications of Mesenchymal Stem Cells in Soft Tissue Augmentation," Aesthet Surg J., 30(6): 838-842 (2010).
Hanson, S. E. et al., "Mesenchymal Stem Cell Therapy for Nonhealing Cutaneous Wounds." Plastic Reconstr. Surg., 125(2): 510-516 (2010).
Lim and Yoo, "Effects of Adipose-derived Stromal Cells and of their Extract on Wound Healing in a Mouse Model." J Korean Med Sci, 25(5): 746-751 (2010).
Yoshimura, K. et al., "Adipose-derived stem/progenitor cells: roles in adipose tissue remodeling and potential use for soft tissue augmentation." Regenerative Medicine, Future 4(2): 265-273 (2009).
Zarandi, P. et al., "Serum-free isolation of adipose tissue derived multipotent mesenchymal stromal cells." Abstracts of the Royan International Congress on Stem Stell Biology & Technology, Yakhteh Medical Journal, vol. 12, Supp. Suppl. 1, pp. 4-42, Abstract No. PS-43 (Summer 2010).
Office Action for U.S. Appl. No. 15/148,821, mailed Jan. 13, 2017, 13 pages.
Supplementary European Search Report for European Application No. 16195005.0, mailed Jan. 27, 2017, 9 pages.
Office Action for U.S. Appl. No. 14/698,763, mailed Jan. 13, 2017, 15 pages.
Bushkalova et al, "Polyelectrolyte scaffolds for cardiac mesenchymal stem cell therapy," Wound Repair and Regeneration, (Nov.-Dec. 2013), vol. 21, No. 6, pp. A59.
Wierenga et al., "Protection against radiation-induced damage to salivary glands by stem cell transplantation," Blood, (Nov. 16, 2002), vol. 100, No. 11, Abstract No. 4121.
International Search Report and Written Opinion for International Application No. PCT/US2017/020492, mailed May 31, 2017, 13 pages.
Rosova, I. et al., "Hypoxic preconditioning results in increased motility and improved therapeutic potential of human mesenchymal stem cells," Stem Cells, vol. 26, pp. 2173-2182 (2008).
Wang, E-T et al., "Regulation of tissue repair and regeneration by electric fields," Chinese Journal of Traumatology, vol. 13, No. 1, pp. 55-61 (2010).
Yew, T-L et al., "Enhancement of wound healing by human multipotent stromal cell conditioned medium: the paracrine factors and p38 Mapk activation," Cell Transplantation, vol. 20, pp. 693-706 (2011). Epub Dec. 2010.

\* cited by examiner

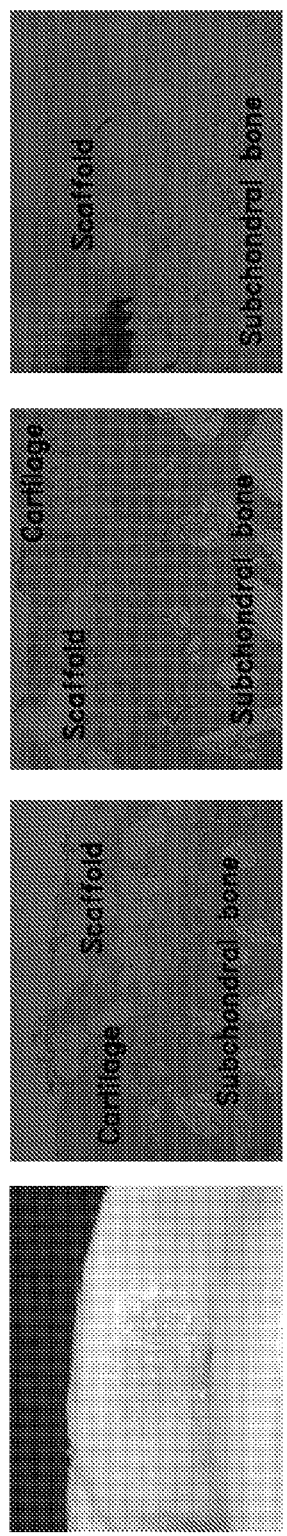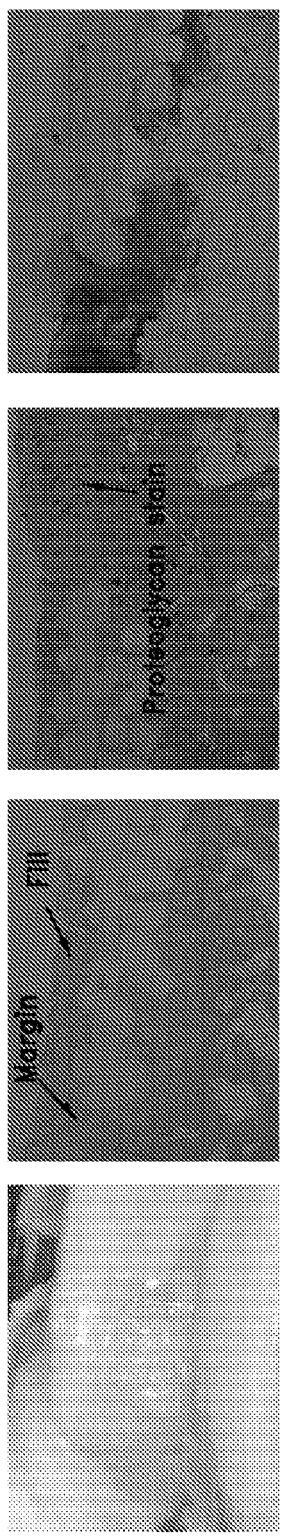

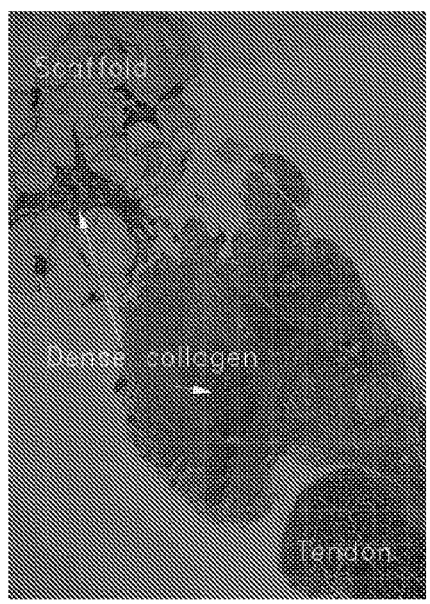 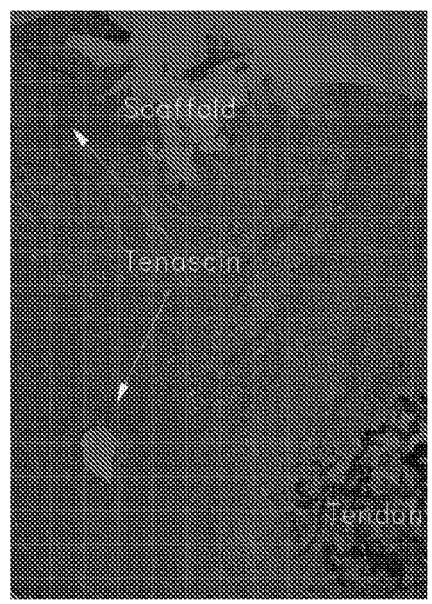
*FIG. 15E*  *FIG. 15F*

COMPOSITIONS AND METHODS FOR TREATING AND PREVENTING TISSUE INJURY AND DISEASE

RELATED APPLICATIONS

This application claims the benefit of U.S. Provisional Application No. 61/703,203, filed on Sep. 19, 2012, the disclosure of which is expressly incorporated by reference herein.

BACKGROUND

Field

Several embodiments of the present invention are directed to novel compositions comprising multipotent cells and/or microvascular tissue, which has been sterilized and/or treated to inactivate any viruses, and methods for their preparation and allogeneic or xenogeneic use in treating or preventing tissue injury and diseases, such as, e.g., arthritis.

Description of the Related Art

Injuries to soft tissues, such as muscles, tendons, ligaments, and joint capsules, occur quite frequently. Such injuries typically result in tissue dysfunction characterized by pain, inflammation and internal tissue stress, and can ultimately result in a functional disability. For example, while sprains to tendons will heal spontaneously, complete tears of a tendon will often lead to disability if not surgically treated. Even despite surgical repair, about 15% of Achilles tendon and 40% of two tendon rotator cuff repairs subsequently fail. Furthermore, the repaired tendon seldom returns to pre-injury strength and function levels.

Tissue repair generally includes several phases, including an initial inflammatory response followed by cellular proliferation and tissue remodeling. Fundamental processes of tissue repair include both fibroplasia and angiogenesis. Fibroblasts activated by inflammatory mediators migrate into the wound, proliferate, and lay down collagen-rich extracellular matrix, while capillaries in the damaged tissue grow towards the repair zone to reestablish blood flow. During the remodeling process, scar tissue is reabsorbed and replaced with denser, oriented collagen, to produce tissue with some of the characteristics of the original tissue.

SUMMARY

A variety of different therapeutic methods to aid in tissue repair have been developed. These include physical structures, such as better sutures, bone anchors, and patches or implants to provide scaffolding for tissue ingrowth. In addition, a variety of growth factors have been used to improve tissue growth and migration to the wound site, as well as to promote angiogenesis. For example, there are reports of improved tendon healing using growth factors such as BMP-2, BMP-12, PDGF-BB, and bFGF in preclinical models.

More recently, efforts have been made to use stem cells to promote wound healing and tissue regeneration. Stem cells are believed to mediate would healing by any of a variety of different mechanisms, including: modulating the inflammatory process; migrating to damaged tissue and recruiting other cells, such as endothelial progenitor cells, necessary for tissue growth; stimulating the proliferation of repair cells; supporting tissue remodeling over scar formation; inhibiting apoptosis; and differentiating into bone, cartilage, tendon, or ligament tissue. There have been a number of reports describing the use of stem cells for the treatment or generation of many different tissues. Much of this work has centered on the use of adipose-derived stem cells and other multipotent cells, because they are easily obtained in large numbers. However, due to concerns that transplanted allogeneic cells or tissue may invoke an immune response and ultimately rejection, or transfer harmful viruses or other pathogens, this work has focused on the use of autologous cells. Unfortunately, however, the use of autologous stem cells is inconvenient. It requires two distinct surgical procedures with associated pain, cost and morbidity, and there are also risks associated with shipping the tissue to a laboratory for processing and delays in treatment of the injured patient.

Clearly, there is a need in the art for new therapeutic compositions of allogeneic stem cells and other multipotent cells useful for the treatment and repair of tissue injury without causing an undesired immune response. The present invention satisfies this need and provides other advantages.

Therefore, there are provided, in several embodiments novel compositions, methods, kits, and cell populations that are useful, such as in the repair and/or regeneration of tissue.

In several embodiments, there are provided compositions comprising isolated multipotent cells or processed microvascular tissue, or a cell membrane obtained from or derived from said cells or tissue, wherein said composition has angiogenic or anti-inflammatory activity, and wherein said composition is sterilized and/or viruses within said composition are inactivated. In particular embodiments, the cells or composition have not been cultured. In particular embodiments, less than or equal to 50% or less than or equal to 10% of the cells present in the composition are viable. In particular embodiments, substantially none of the cells present in said composition are viable. In certain embodiments, at least 1% of said cells exclude trypan blue. In particular embodiments, the composition is dried, lyophilized or cryopreserved. In related embodiments, the composition, including the sterilized, dried, lyophilized, or cryopreserved composition, retains measurable angiogenic or anti-inflammatory activity when stored at approximately room temperature for at least one month. In certain embodiments, the composition comprises an excipient.

In several embodiments, the compositions disclosed herein further comprise an implantable scaffold or matrix, which may be, e.g., a bone-derived implant, a biofiber scaffold, a porous resorbable polymer, a hydrogel, a putty comprising tissue product, or a suture. In particular, cells, tissue or cell membrane are present on a bone, tendon, or dermal facing surface of said implantable scaffold or matrix.

In certain embodiments, a composition of the present invention is formulated for intravenous administration. However, other routes of administration can be used in additional embodiments, including direct administration (either to a tissue surface or by direct injection), intraarterial administration, systemic administration and the like.

In several embodiments, the cells or tissue were obtained from a mammalian donor, optionally a human. In one embodiment, the donor was a healthy mammal at the time the cells or tissue were obtained. In certain embodiments, the cells comprise stem cells or progenitor cells.

In several embodiments, there are provided methods of preparing a composition comprising isolated multipotent cells, wherein said composition has angiogenic or anti-inflammatory activity, said method comprising: dissociating a tissue sample obtained from a donor mammal to release a plurality of multipotent cells therein; separating a plurality of the released multipotent cells from one or more other tissue components to produce a composition comprising isolated multipotent cells; optionally drying, lyophilizing, or cryopreserving the composition before or after sterilization; sterilizing the composition and/or inactivating virus present in the composition, before or after the optional drying, lyophilizing, or cryopreserving of the composition, wherein the sterilized composition retains measurable angiogenic or anti-inflammatory activity. In several embodiments, the cells or composition are not cultured. In certain embodiments, the method optionally further comprises filtering the released cells or composition, e.g., which may be prior to sterilization or drying, lyophilizing, or cryopreserving. In certain embodiments, the dissociation comprises contacting the tissue sample with one or more proteases. In particular embodiments, the one or more proteases does not comprise collagenase. In certain embodiments, the one or more proteases comprises or consists of: collagenase type 1 and either dispase or thermolysin; or MMP2, MMP 14 and either dispase or thermolysin. Combinations of these proteases (or other functional equivalents) can be used. In additional embodiments, the dissociating or separating comprises ultrasonic agitation, filtration, or use of a density gradient. In one embodiment, the tissue is adipose-derived tissue, and the ultrasonic agitation, filtration or use of a density gradient separates said released multipotent cells from adipocytes.

In additional embodiments, there are provided methods of preparing a composition comprising processed microvascular tissue, wherein said composition has angiogenic or anti-inflammatory activity, said method comprising: dissociating a microvascular tissue sample obtained from a donor mammal to produce a composition comprising dissociated microvascular tissue; removing one or more tissue components from the composition comprising dissociated microvascular tissue; optionally drying, lyophilizing, or cryopreserving the composition before or after sterilization; and sterilizing the composition and/or inactivating virus present in the composition before or after the optional drying, lyophilizing, or cryopreserving, wherein the sterilized composition retains measurable angiogenic or anti-inflammatory activity. In particular embodiments, the cells or composition are not cultured. In particular embodiments, the method further comprises filtering the composition. In particular embodiments, the dissociation comprises contacting the tissue sample with one or more proteases. In certain embodiments, the one or more proteases does not comprise collagenase. In certain embodiments, the one or more proteases comprises or consists of: collagenase type 1 and either dispase or thermolysin; or MMP2, MMP 14 and either dispase or thermolysin. In certain embodiments, the dissociation or removing comprises ultrasonic agitation, filtration, or use of a density gradient. In particular embodiments, the microvascular tissue is adipose-derived tissue, and said ultrasonic agitation, filtration or use of a density gradient removes adipocytes from the composition.

In an additional embodiment, the present invention provides a moisture impermeable container comprising a sterile, dry composition, wherein said composition comprises isolated multipotent cells or processed microvascular tissue, or a cell membrane comprising said cells or tissue or obtained from said cells or tissue, said composition has angiogenic or anti-inflammatory activity, said composition is sterilized and/or viruses within said composition are inactivated, and said composition retains measurable angiogenic or anti-inflammatory activity when stored at approximately room temperature for at least one month. In certain embodiments, the cells or composition have not been cultured. In particular embodiments, less than or equal to 50% or less than or equal to 10% of the cells present in said composition are viable. In certain embodiments, substantially none of the cells present in said composition are viable. In particular embodiments, at least 1% of said cells exclude trypan blue. In particular embodiments, the composition comprises an excipient.

In particular embodiments of the moisture impermeable container, the composition further comprises an implantable scaffold or matrix. In particular embodiments, the implantable scaffold or matrix is a bone-derived implant, a biofiber scaffold, a porous resorbable polymer, a hydrogel, a putty comprising tissue product, or a suture. In certain embodiments, the cells, tissue or cell membrane are present on a bone, tendon or dermal facing surface of said implantable scaffold or matrix.

In one embodiment of the moisture impermeable container, the composition is formulated for intravenous administration.

In particular embodiments of the moisture impermeable container of the invention, the cells or tissue were obtained from a mammalian donor, optionally a human. In particular embodiments, the donor was a healthy mammal at the time the cells or tissue were obtained. In certain embodiments, the cells comprise stem cells or progenitor cells. In certain embodiments, the container is a vial comprising a hermetic seal. In various embodiments, the container is present within a sealed package comprising a sterile interior.

In another related embodiment, the present invention provides a method of treating or preventing an injury or disease, or promoting tissue regeneration, in a mammal, comprising providing to said mammal a composition of the present invention or a composition prepared according to a method of the present invention. In particular embodiments, the composition is surgically implanted into the mammal. In certain embodiments, the composition is implanted within or adjacent to a site of injury or disease in said mammal. In related embodiments, the composition is provided to said mammal intravenously. In certain embodiments, the injury is present in a soft tissue. In particular embodiments, the injury is present in a tendon, a ligament, skin, a bone, cartilage, a disc, or microvascular tissue. In particular embodiments, the injury or disease is an ischemic injury, a reperfusion injury, a microvascular injury, or inflammation. In certain embodiments, the disease is arthritis, such as e.g., osteoarthritis or rheumatoid arthritis.

In additional embodiments, there are provided compositions comprising multipotent cells and one or more vessel wall and/or extracellular matrix components. In another embodiment, the present invention includes a sterilized composition comprising multipotent cells. In further embodiments, the present invention includes a composition comprising multipotent cells that exclude trypan blue but will not proliferate. In a further embodiment, the present invention includes a composition comprising multipotent cells and one or more vessel wall extracellular matrix components. In another embodiment, the present invention includes a sterilized composition comprising multipotent cells. In a further embodiment, the present invention includes a composition comprising multipotent cells that exclude trypan blue but will not proliferate. In a related embodiment, the present invention includes a composition comprising sterilized multipotent cells that exclude trypan blue but will not proliferate. In certain embodiments of compositions of the present invention, at least 50% or at least 90% of the cells present in the composition exclude trypan blue but will not proliferate. In certain embodiments, the composition comprises multipotent cells. In one embodiment, at least 50% or at least 90% of the multipotent cells present in the composition exclude trypan blue but will not proliferate. In particular embodiments, less than or equal to 50% or less than or equal to 10% of the total cells present in the composition are viable. In particular embodiments, substantially none of the cells present in said composition are viable. In certain embodiments of any of the compositions or methods of the present invention, at least 1% or at least 5%, or at least 10%, or at least 20%, at least 50%, or at least 90% of said cells exclude trypan blue.

In an additional embodiment, the present invention includes a sterilized composition comprising two or more components of multipotent cells. In certain embodiments, the composition comprises five or more or ten or more components of multipotent cells. In another related embodiments, the present invention includes a composition comprising cell membrane and proteins from multipotent cells. In particular embodiments, the composition does not comprise any viable cells or does not comprise any intact cells.

In addition, the present invention provides that any of the compositions of the invention may be used in treating or preventing an injury or disease in a subject, including any of the injuries or conditions described herein, wherein said multipotent cells are not autologous to said subject.

The methods summarized above and set forth in further detail below describe certain actions taken by a practitioner; however, it should be understood that they can also include the instruction of those actions by another party. Thus, actions such as "administering microvascular tissue" include "instructing the administration of microvascular tissue."

BRIEF DESCRIPTION OF THE DRAWINGS

FIG. 13A depicts data related to the strength, elastic modulus, and toughness (as compared to control contralateral bone) after administration of a scaffold with or without microvascular tissue. FIG. 13B depicts histologic data regarding bone regeneration after administration of scaffold alone. FIG. 13C depicts histologic data regarding bone regeneration after administration of scaffold in combination with microvascular tissue.

FIGS. 14A-14H relate to the regeneration of cartilage after implantation of microvascular tissue. FIG. 14A shows a macroscopic image of cartilage treated with scaffold alone, while FIGS. 14B, 14C, and 14D show images related to the fill in of the induced cartilage defects, the proteoglycan retention and matrix staining (respectively) in cartilage treated with scaffold alone. FIG. 14E shows a macroscopic image of cartilage treated with scaffold supplemented with microvascular tissue, while FIGS. 14F, 14G, and 14H show images related to the fill in of the induced cartilage defects, the proteoglycan retention and matrix staining (respectively) in cartilage treated with scaffold supplemented with microvascular tissue.

FIGS. 15A-15F related to repair of abraded tendon using microvascular tissue. FIGS. 15A and 15B depict, respectively, Masson's Trichrome staining or Tenascin immunohistochemistry of abraded and untreated tendon. FIGS. 15C and 15D depict, respectively, Masson's Trichrome staining or Tenascin immunohistochemistry of abraded tendon treated with scaffold alone. FIGS. 15E and 15F depict, respectively, Masson's Trichrome staining or Tenascin immunohistochemistry of abraded tendon treated with scaffold supplemented with microvascular tissue.

DETAILED DESCRIPTION

Figure 1:
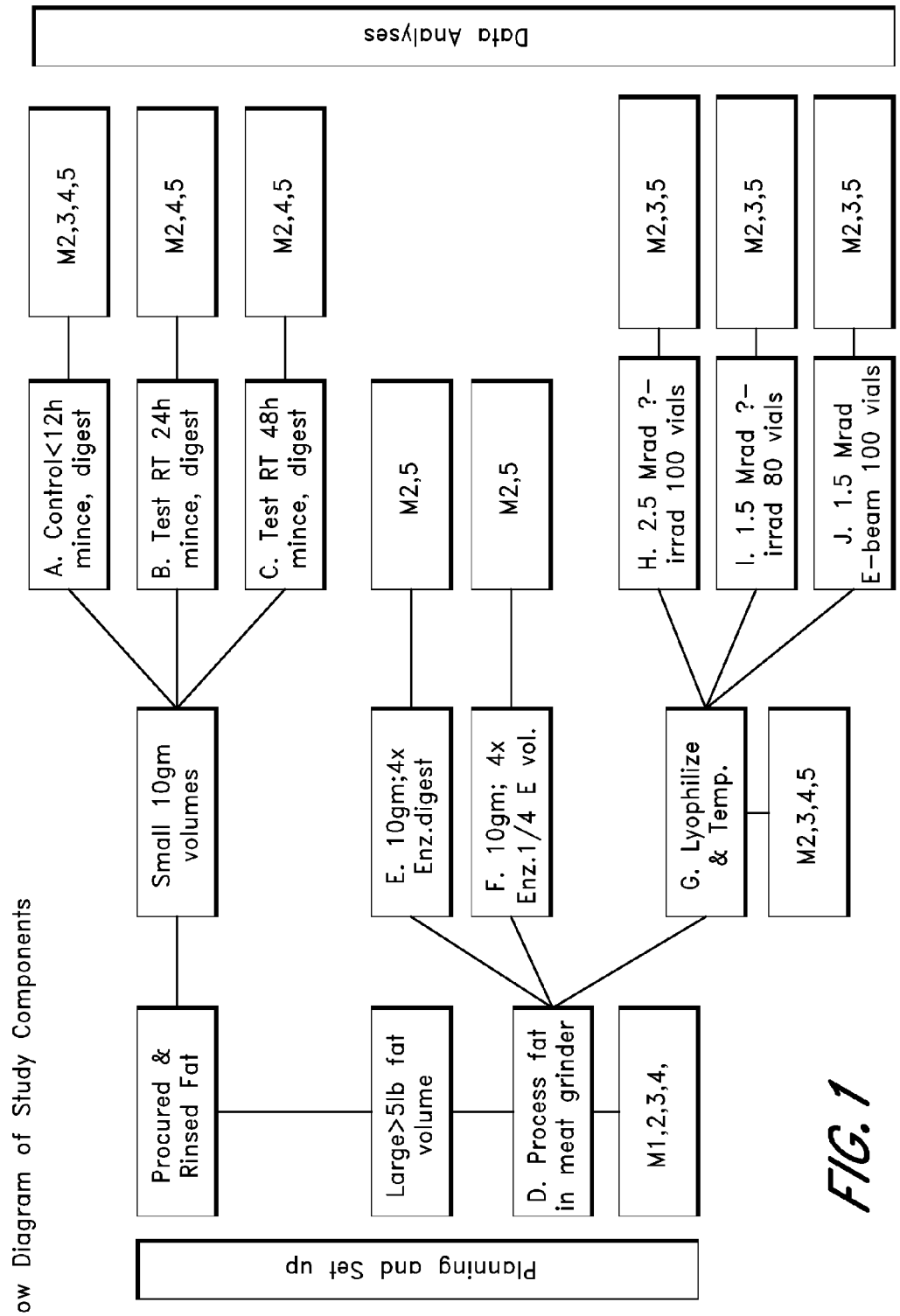
FIG. 1 provides a schematic diagram of the studies described in Example 1.

The present invention is based, in part, on the development of novel methods for processing microvascular tissue to produce a composition comprising isolated multipotent cells or processed microvascular tissue, or a cell membrane comprised of said cells or tissue. In various embodiments, the cells or tissue are not cultured during these procedures. Advantageously, the composition has angiogenic or anti-inflammatory activity. In several embodiments, the composition is sterilized and/or viruses within said composition are inactivated during the procedures, yet the composition still displays unexpected therapeutic efficacy.

The novel compositions produced by the methods of the present invention offer advantages over prior processed microvascular tissue and multipotent cell compositions, including advantages associated with treating or preventing an injury, e.g., a soft tissue injury, in a subject. These advantages include (but are not limited to): (1) the ability to use the compositions of the present invention for the allogeneic or xenogeneic treatment of subjects; (2) compositions of the present invention produce a reduced immune response and reduced likelihood of rejection; (3) compositions of the present invention have anti-inflammatory activity; (4) compositions of the present invention have angiogenic activity; (5) compositions of the present invention are sterile and/or are not contaminated by harmful viruses; and (6) compositions of the present invention may be stably stored prior to use and/or are ready for immediate use. In short, these compositions conveniently provide all the mechanisms of action inherent in traditional, viable stem or multipotent cell preparations except for differentiation into tissues. In the following description, certain specific details are set forth in order to provide a thorough understanding of various embodiments of the invention. However, one skilled in the art will understand that the invention may be practiced without these details.

DEFINITIONS

Unless defined otherwise, all technical and scientific terms used herein have the same meaning as commonly understood by those of ordinary skill in the art to which the invention belongs. For the purposes of the present invention, the following terms are defined below.

The words "a" and "an" denote one or more, unless specifically noted.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about," it is specifically contemplated that the term about can be omitted.

Unless the context requires otherwise, throughout the present specification and claims, the word "comprise" and variations thereof, such as, "comprises" and "comprising" are to be construed in an open, inclusive sense, that is as "including, but not limited to".

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the terms "function" and "functional", and the like, refer to a biological, enzymatic, or therapeutic function.

An "increased" or "enhanced" amount is typically a "statistically significant" amount, and may include an increase that is 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 2.1, 2.2, 2.3, 2.4, etc.) an amount or level described herein.

A "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

By "obtained from" is meant that a sample such as, for example, a cell or tissue, is isolated from, or derived from, a particular source, such as a desired organism or a specific tissue within a desired organism.

As used herein, the term "isolated", e.g., with respect to a multipotent cell, means removed from its natural environment. For example, a cell is isolated if it is separated from some or all of the coexisting materials in its natural environment.

The term "processed microvascular tissue" as used herein refers to microvascular tissue that is dissociated as described herein.

The term "cryopreserved" as used herein refers to multipotent cell or processed microvascular tissue compositions that are frozen, e.g., at low temperature. Processed microvascular tissue and cryopreserved multipotent cell and microvascular tissue compositions have a variety of biological properties, including anti-inflammatory activity and angiogenic activity.

"Multipotent cells" refers to cells that maintain the capacity to differentiate into two or more different specialized cell types. "Multipotent cells" include stem cells and multipotent progenitor cells. As used herein, the term "multipotent cell" refers to a cell's original capacity to differentiate into two or more different specialized cell types prior to it being sterilized or preserved according to a method described herein. Examples of multipotent cells include, but are not limited to, mesenchymal stem cells, embryonic stem cells, neural stem cells, endothelial progenitor cells, adipose-derived stem cells, and umbilical cord stem cells. It is understood that following sterilization or preservation according to the methods described herein, a multipotent cell may lose its capacity to grow or differentiate.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent or emulsifier which has been approved by the United States Food and Drug Administration as being acceptable for use in humans or domestic animals.

A "pharmaceutical composition" refers to a formulation of a composition of the invention and a medium generally accepted in the art for the delivery of a therapeutic agent to mammals, e.g., humans. Such a medium includes any pharmaceutically acceptable carriers, diluents or excipients therefore.

As used herein, unless the context makes clear otherwise, "treatment," and similar words such as "treated," "treating" etc., indicates an approach for obtaining beneficial or desired results, including clinical results. Treatment can involve optionally either the reduction or amelioration of symptoms of an injury, disease or condition, or the delaying of the progression of the injury, disease or condition. Administration of a composition described herein may, in some embodiments, treat one or more of such symptoms.

As used herein, unless the context makes clear otherwise, "prevention," and similar words such as "prevented," "preventing" etc., indicates an approach for preventing, inhibiting or reducing the likelihood of the onset or recurrence of an injury, disease or condition. It also refers to preventing, inhibiting or reducing the likelihood of the occurrence or recurrence of one or more symptoms of an injury, disease or condition, or optionally an approach for delaying the onset or recurrence of an injury, disease or condition or delaying the occurrence or recurrence of one or more symptoms of an injury disease or condition. As used herein, "prevention" and similar words also includes reducing the intensity, effect, symptoms and/or burden of an injury, disease or condition.

As used herein, an "effective amount" or a "therapeutically effective amount" of a composition is that amount sufficient to affect a desired biological effect, such as, e.g., beneficial clinical results.

The terms "autologous transfer," "autologous transplantation," and the like refer to treatments wherein the tissue donor is also the recipient of the composition produced from the tissue.

The terms "allogeneic transfer," "allogeneic transplantation," and the like refer to treatments wherein the tissue donor is of the same species as the recipient of the composition produced from the tissue, but is not the same individual.

The terms "xenogeneic transfer," "xenogeneic transplantation," and the like refer to treatments wherein the tissue donor is of a different species than the recipient of the composition produced from the tissue.

Methods of Producing Stem Cell and Microvascular Tissue Compositions

Aspects of the present invention relate to novel methods of processing vascular, e.g., microvascular, tissue to produce a composition comprising multipotent cells or fragments thereof. In particular embodiments, the composition further comprise one or more additional tissue components. Accordingly, the term "processed microvascular tissue composition" refers to compositions of the present invention, which may or may not comprise intact multipotent cells. In particular embodiments, a microvascular tissue composition of the present invention does not comprise any intact multipotent cells or does not comprise any live multipotent cells or does not comprise any live cells. In certain embodiments, a microvascular tissue composition of the present invention comprises fragments or cell membranes of multipotent cells. A "composition comprising multipotent cells" or "multipotent cell composition" of the present invention may comprise live and/or dead multipotent cells.

Several embodiments provide novel methods for producing multipotent cell and microvascular tissue compositions, including those useful in the treatment and prevention of various injuries, disease or pathological conditions, e.g., a soft tissue injury. In particular embodiments, the methods of the present invention include sterilizing the isolated multipotent cells or microvascular tissue composition and/or inactivating viruses within said cells or tissue. It is a surprising and unexpected finding that such sterilized multipotent cell and microvascular tissue compositions retain desirable biological properties, including properties useful in treating or preventing injury, disease and other pathological conditions.

The multipotent cell and microvascular tissue compositions of the present invention may be prepared from any mammalian tissue, e.g., tissue obtained from a mammal, such as a human, a non-human primate, a dog, a cat, or a horse. The compositions of the present invention may be used to treat an autologous, allogeneic or xenogeneic subject. Accordingly, tissue may be obtained from the subject to be treated, or from a different donor animal, which may be the same or a different species as the subject to be treated. In particular embodiments, the tissue is obtained from an allogeneic donor of the same species as the subject to be treated, e.g., a human or non-human mammalian donor. In particular embodiments, a donor animal is a healthy donor.

In various embodiments, multipotent cell or microvascular tissue compositions are prepared from any of a number of different tissues. In particular embodiments, the tissue is non-embryonic tissue. For example, in particular embodiments, the tissue used to prepare the compositions of the present invention is a vascular tissue or a microvascular tissue, such as, e.g., adipose tissue, skin, bone, tendon tissue, post-partum tissue (e.g., umbilical cord tissue or placental tissue), bone marrow, or muscle tissue.

In certain embodiments, compositions of the present invention may be prepared by a method comprising: dissociating a tissue sample to release cells and/or other tissue components; separating at least a portion of the released cells and/or tissue components from one or more other tissue components; and sterilizing the separated cells and/or tissue components and/or treating the separated cells and/or tissue components to inactivate viruses therein. In certain embodiments, the separated cells and/or tissue components are dried, lyophilized, frozen, or cryopreserved before, during or after being sterilized or treated to inactivate viruses. In particular embodiments, the separated cells and/or tissue components are sterilized or treated to inactivate viruses after being dried, lyophilized, frozen, or cryopreserved. In related embodiments, the separated cells and/or tissue components are sterilized or treated to inactivate viruses after being contacted with a cryoprotectant, e.g., a cryoprotectant that protects cells from sterilizing radiation. Cryoprotectants can protect cell components by stabilizing proteins, quenching free radicals, and resisting oxidation. Damage can be further minimized by cooling the composition during radiation, removing oxygen from the composition (e.g., drying the composition and/or irradiating in a vacuum or inert atmosphere).

In related embodiments, methods of the present invention comprise: dissociating a tissue sample obtained from a donor mammal to release a plurality of multipotent cells therein; separating a plurality of the released multipotent cells from one or more other tissue components to produce a composition comprising isolated multipotent cells; and sterilizing the composition comprising isolated multipotent cells and/or inactivating virus present in the composition comprising isolated multipotent cells. In particular embodiments, the composition comprising multipotent cells is dried, lyophilized, frozen, or cryopreserved before, during or after being sterilized or treated to inactivate viruses. In particular embodiments, the separated cells and/or tissue components are sterilized or treated to inactivate viruses after being dried, lyophilized, frozen, or cryopreserved. In related embodiments, the separated cells and/or tissue components are sterilized or treated to inactivate viruses after being contacted with a cryoprotectant, e.g., a cryoprotectant that protects cells from sterilizing radiation.

In further related embodiments, methods of the present invention comprise: dissociating a tissue sample obtained from a donor mammal to release a plurality of tissue components therein; separating a plurality of released tissue components to produce a composition comprising one or more tissue components; and sterilizing the composition and/or inactivating virus present in the composition. In particular embodiments, the composition is dried, lyophilized, frozen, or cryopreserved before, during or after being sterilized or treated to inactivate viruses. In particular embodiments, the separated cells and/or tissue components are sterilized or treated to inactivate viruses after being dried, lyophilized, frozen, or cryopreserved. In related embodiments, the separated cells and/or tissue components are sterilized or treated to inactivate viruses after being contacted with a cryoprotectant, e.g., a cryoprotectant that protects cells from sterilizing radiation.

In certain embodiments, tissue components comprise one or more multipotent cells, differentiated cells, components of the extracellular matrix, growth factors, angiogenic agents, anti-inflammatory agents, cytokines, chemokines, and/or differentiation agents. Extracellular matrix components include but are not limited to extracellular matrix proteins, such as various collagens, fibronectin, vitronectin, and thrombospondin, and others described herein.

Tissue samples may be obtained from a subject or donor by a variety of different methods, including surgery, lipoaspiration, biopsy or needle biopsy. A donor may be alive or dead, e.g., recently deceased.

Tissue may be dissociated by various methods, including both mechanical and/or enzymatic processing. For example, tissue may be dissociated by mechanical force (mincing or shear forces), enzymatic digestion with single or combinatorial proteolytic enzymes, such as a matrix metalloprotease and/or neutral protease, for example, collagenase, trypsin, dispase, LIBERASE (Boehringer Mannheim Corp., Indianapolis, Ind.), hyaluronidase, and/or pepsin, or a combination of mechanical and enzymatic methods. In particular embodiments, methods of the present invention do not employ the use of a collagenase.

In certain embodiments, enzymatic digestion methods employ a combination of enzymes, such as a combination of a matrix metalloprotease and a neutral protease. In particular embodiments, the matrix metalloprotease may be a collagenase, and the neutral protease may be thermolysin or dispase. Collagenase may be type 1, 2, 3, or 4 (MMP 1, 8, 13, 18). In particular embodiments, enzymatic digestion methods employ a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes known in the art for cell dissociation include papain, deoxyribonucleases, serine proteases, such as trypsin, chymotrypsin, gelatinases, or elastase, that may be used either on their own or in combination with other enzymes such as matrix metalloproteases, mucolytic enzymes, and neutral proteases. In certain embodiments, a combination of enzymes comprises or consists of Type 1 collagenase with either dispase or thermolysin, Liberase, and/or Vitacyte. In certain embodiments, a combination of enzymes comprises or consists of Type 1 collagenase with either dispase or thermolysin, Liberase, and/or Cizyme. In particular embodiments, a collagenase is not used, either alone or in combination with one or more additional enzymes. In certain embodiments, MMP 2 and/or 14 are used instead of MMP 1 (alone or in any of the combinations described herein).

The temperature and period of time tissues or cells are in contact with proteases to achieve dissociation is known and may be readily determined by one of skill in the art. The enzymatic digestion process can be adjusted to increase or decrease cell dissociation. For example, if more complete cell dissociation is desired, more than one enzyme can be included or digestion time can be increased. While cell viability need not be maintained, in some embodiments it is generally desired that cellular membranes remain generally intact to preserve membranes containing attachment and signaling molecules even if some cell lysis occurs during enzymatic digestion. Thus, the use of enzymes such as lipidases may not be useful in such a process, according to one embodiment of the present invention.

Alternatively, or in addition to enzymatic treatment, tissue can be dissociated using a non-enzymatic method. For example, tissue can be dissociated using physical or chemical means, including the use of chelators, ultrasonic agitation, ultrasound (e.g., to lyse or remove adipocytes), or mechanical cell dissociation.

In particular embodiments where the tissue is bone, the bone is demineralized prior to enzymatic (or other) processing to free cells from the collagen matrix. In particular embodiments, the bone is demineralized using EDTA (as opposed to a solvent to defat the tissue followed by acid to remove bone minerals). In certain embodiments, methods of processing tissue, e.g., bone, do not include one or more of the following: solvent extraction of fats and/or cells, cryomilling to reduce particle size, and/or acid demineralization.

Following tissue dissociation, the dissociated tissue can be further treated to isolate or separate desired tissue components, e.g., multipotent cells (and/or other desired cellular or non-cellular tissue components), from undesired tissue components. These methods may be used, e.g., to remove undesired cells or molecules, such as red blood cells, adipocytes, other differentiated cells, or lipids. A variety of methods may be used to separate multipotent cells and other desired tissue components from undesired cells or tissue components, such as, e.g., filtration (e.g., a 20 micron pore size filter would pass multipotent cells but retain many adipocytes or muscle cells), centrifugation (adipocytes and lipids float, while multipotent cells are pelleted), or density gradients (gradients may be used to pellet red cells and to suspend multipotent cells at different levels than unwanted cells). The particular method used may depend, in part, upon the source of tissue being processed. For example, if the tissue source is adipose tissue, the dissociated tissue is optionally centrifuged at relatively low force to separate lipids, adipocytes, and some pre-adipocytes from other components of the microvascular tissue, while a density gradient is optionally used when isolating multipotent cells from bone marrow. In other embodiments, muscle cell isolation protocols, such as the use of density gradient centrifugation, may be used to further treat muscle tissue following enzymatic digestion to remove muscle cells and enrich for desired cells.

In certain embodiments, a composition of the present invention is also filtered, e.g., to remove clumps. For instance, filtration, e.g., with a 20 to 50 micron pore size filter, to remove large clumps may be performed during preparation of a composition for intravenous injection, to avoid clogging of capillaries. In particular embodiments, filtration is performed after dissociation and prior to use, e.g., after dissociation and prior to lyophilization or sterilization.

Depending on the embodiment, the multipotent cell composition and microvascular tissue compositions are optionally frozen or dried for storage or preservation, e.g., dried (e.g., freeze-dried or spray-dried), cryopreserved, or frozen. Any appropriate excipient can be used when preserving compositions of the invention, including sugars (e.g., trehalose, mannitol, sucrose), polyalcohols (e.g., polyethylene glycol), aldehydes, proteins (e.g., albumin), amino acids (e.g., glycine), surfactants (e.g., Tween 20), DMSO, and/or permanganates. In several embodiments, no excipient is used.

Cells and their active components can be protected in part from damage by ionizing radiation by several methods. Antioxidants or free radical scavengers can be very effective. Agents that immobilize macromolecules such as the sugars used in lyophilization and the drying process itself increase the odds that disrupted chains will recombine in their original chemical structure. Removal of water, air and other sources of oxygen will reduce the oxidation of proteins or other biologically active species. Freezing the composition during radiation also reduces the odds of cleaved molecules recombining inappropriately. Finally, the much greater concentration of excipients than cells or active molecules in the cells means that there will be fewer cleavages of active compounds simply due to mass action effects.

Freeze drying (e.g., lyophilization) typically involves four steps: pretreatment, freezing, primary drying, and secondary drying. Pretreatment can include concentration adjustment or the addition of one or more excipients. Following pretreatment, the multipotent cell or microvascular tissue composition is frozen. The freezing step is typically done in a carefully controlled manner (e.g., at a rate of cooling of between about $-0.5°$ C. per minute to about $-50°$ C. per minute) to preserve cell structure, however cell viability need not be preserved. In some embodiments, the multipotent cell or microvascular tissue composition is frozen at a rate of cooling of about $-10°$ C. per minute. The rate of cooling can be adjusted based on the particular cells or tissue and excipients used. The multipotent cell or microvascular tissue composition can be frozen using any appropriate means, including using mechanical refrigeration and/or exposing a container containing the composition to dry ice or liquid nitrogen until it reaches a temperature suitable for freeze drying. During the primary drying step, the temperature and pressure are adjusted to provide conditions suitable to cause sublimation of water from the multipotent cells or microvascular tissue. The specific temperature and pressure can be adjusted to accommodate the excipient used and/or the concentration of the cells or microvascular tissue. During the secondary drying step, the temperature and pressure can be further adjusted to facilitate the removal of unfrozen water from the multipotent cells or microvascular tissue. The final water content following the secondary drying step is preferably between about 1% and about 4% by weight (including about 1% to about 2%, about 2% to about 3%, about 3% to about 4%, about 4% to about 5%, and overlapping ranges thereof), but can be adjusted in order to maximize shelf life or biological activity.

In some embodiments, the multipotent cell or microvascular tissue composition is spray dried. Prior to spray drying, the multipotent cell or microvascular tissue composition can be pretreated similarly to multipotent cell or microvascular tissue composition that is to be freeze dried, with the excipients being chosen as appropriate for spray drying rather than freeze drying. During spray drying, the multipotent cells or microvascular tissue is atomized into droplets and exposed to heated air in a drying chamber. In one embodiment, an excipient is a sugar that does not melt under the temperatures utilized. In particular embodiments, an excipient is an antioxidant, such as BHA, BHT, and propyl gallate, for example.

In some embodiments, multipotent cell and microvascular tissue compositions are not processed by drying, but instead are cryopreserved. Methods for cryopreserving cells and tissue are known. For example, cells or microvascular tissue compositions may be mixed with one or more excipients or cryoprotectants (e.g., DMSO, PEG, albumin, or sugar) and cooled in a carefully controlled manner. In some embodiments, cooling is done in two or more stages in which the first stage is done in a controlled manner (e.g., reducing the temperature by $1°$ C. per minute) to an intermediate temperature (e.g., $-30°$ C.), with the second stage transferring cells or tissue at the intermediate temperature to a colder storage temperature (e.g., $-196°$ C.).

Cryopreserved multipotent cell and vascular tissue compositions may be stored at a temperature suitable for maintaining the cryopreserved state (e.g., from about $-30°$ C. to $-196°$ C.). Freeze-dried or spray-dried processed cells or microvascular tissue can be stored in a wider variety of conditions than cryopreserved cells, live cells, or fresh tissue. Suitable temperatures for the storage for processed cells or microvascular tissue include temperatures from about $-100°$ C. to about $45°$ C. In some embodiments, freeze-dried or spray-dried processed cells or microvascular tissue can be stored at room temperature.

In various embodiments, the shelf life of the provided processed cells or microvascular tissue is at least about one week, at least about one month, at least about two months, at least about six months, or greater while maintaining one or more biological activities. In particular embodiments, the composition retains measurable angiogenic or anti-inflammatory activity when stored at approximately 4° C. for at least one about month, at least about two months, at least about four months, at least about six months, or at least one year. In particular embodiments of kits and compositions described herein, the composition retains measurable angiogenic or anti-inflammatory activity when stored at approximately −20° C. for at least one about month, at least about two months, at least about four months, at least about six months, or at least about one year. In particular embodiments, the measurable angiogenic or anti-inflammatory activity is at least about 10%, at least about 20%, at least about 30%, at least about 40%, at least about 50%, at least about 60%, at least about 70%, at least about 80%, or at least about 90% of the activity prior to storage, when measured in an in vivo or in vitro assay, including any of those described herein.

Dissociated tissue, or cells and other tissue components isolated therefrom, including the resulting compositions, are optionally sterilized, e.g., to reduce or eliminate contamination by microorganisms, such as, e.g., bacterial, viruses, and fungi, or prions. In particular embodiments, compositions comprising multipotent cells and/or other tissue components, are sterilized using irradiation. Methods of sterilization exist using radiation such as electron beams, X-rays, gamma rays, or ultraviolet radiation. In particular embodiments, sterilization is performed by exposing dissociated tissue, or cells and other tissue components isolated therefrom, to gamma radiation at a dosage in the range of about 0.5 to about 5.0 Mrad, or about 1.0 to about 3.0 Mrad, or about 1.0 Mrad, or about 1.5 Mrad, or about 2.0 Mrad, or about 2.5 Mrad, or about 3.0 Mrad, or about 3.5 Mrad, or about 4.0 Mrad, or about 4.5 Mrad, or about 5.0 Mrad (or any amount of gamma radiation between those values). In particular embodiments, sterilization is performed by exposing dissociated tissue, or cells and other tissue components isolated therefrom, to electron beam radiation at a dosage in the range of about 0.5 to about 5.0 Mrad, or about 1.0 to about 3.0 Mrad, or about 1.0 Mrad, or about 1.5 Mrad, or about 2.0 Mrad, or about 2.5 Mrad, or about 3.0 Mrad, or about 3.5 Mrad, or about 4.0 Mrad, or about 4.5 Mrad, or about 5.0 Mrad (or any amount of gamma radiation between those values). It is often easier to measure the amount of radiation to which the compositions are exposed. In particular embodiments, E-beam or gamma radiation levels for sterilization are about 9 to about 30 kGy, or about 20 to about 30 kGy, or about 9 to about 17 kGy (or any amount of radiation between those values). In addition, dissociated tissue, or cells and other tissue components isolated therefrom, may be treated to inactivate viruses. Methods of inactivating viruses are known in the art, including the use of irradiation, as described above for sterilization. Other methods of inactivating viruses may be used, including acid or base treatments, bleach, aldehyde or ethylene oxide solutions, or heat. It is understood that cryprotectants and other excipients used for lyophilizing or freezing the composition may also protect against radiation. For example, sugars and albumin (or other stabilizing proteins) along with the low temperature protect against radiation damage to cells. Accordingly, in particular embodiments, sterilization or viral inactivation is performed after lyophilization.

Additionally, because viability is not required for suitability of the processed or cryopreserved multipotent cell or microvascular tissue compositions for therapeutic use, the preservation process and storage need not be adjusted to maintain viability. The percentage of viable cells in the provided multipotent cell or microvascular tissue compositions before processing, sterilization, or cryopreservation can be up to 100%. After processing, sterilization, or cryopreservation, it may be less than about 50%, e.g., less than about 40%, less than about 30%, less than about 20%, less than about 10%, or less than about 1%. In some embodiments, the provided processed multipotent cell or microvascular tissue composition contains no viable cells after processing, sterilization, or cryopreservation. In several embodiments, the processed or cryopreserved multipotent cell or microvascular tissue compositions are used in the therapeutic repair and/or regeneration of, for example, soft tissue. In additional embodiments, the processed or cryopreserved multipotent cell or microvascular tissue compositions are used in the therapeutic repair and/or regeneration of hard tissue.

Furthermore, to reduce the likelihood of microbial contamination, donors can be screened for a predetermined list of microbial organisms (e.g., HIV, HPV, EBV, TB, etc.) prior to tissue procurement or processing. Screening can be done using known techniques, such as detecting the presence of a microbial nucleic acid using polymerase chain reaction, or by detecting the presence of a molecule associated with a particular microbe by ELISA. Microbially contaminated microvascular tissue can be excluded from use, according to some embodiments of the present invention. In addition, processed or cryopreserved tissue can be produced using aseptic or sterile techniques.

In particular embodiments, the methods of the present invention do not include culturing the dissociated cells or microvascular tissue.

Isolated Stem Cell and Microvascular Tissue Compositions

The methods of the present invention produce unique multipotent cell and microvascular tissue compositions. The multipotent cell and microvascular tissue compositions provided herein comprise, in several embodiments, minimally processed, uncultured cells or uncultured microvascular tissue (or components thereof) that may include a mixture of stem and/or progenitor cells produced from the dissociation (e.g., by enzymatic digestion) of a microvascular tissue (e.g., adipose, tendon, or muscle tissue). Processed multipotent cell and microvascular tissue compositions can include additional molecules (e.g., whole or fragmented extracellular matrix molecules or growth factors). In addition, processed multipotent cell and microvascular tissue compositions may, depending on the embodiment, comprise fragments or membranes of multipotent cells. Furthermore, processed microvascular tissue may or may not comprise intact multipotent cells.

As noted above, the methods of the present invention may be used to prepare a composition comprising multipotent cells or processed microvascular tissue, alone or in combination with one or more additional cell types and/or other components.

In particular embodiments, the additional cell type is a stromal, epithelial, or blood-derived cell, including, but not limited to, fibroblasts, keratinocytes including follicular outer root sheath cells, endothelial cells, pericytes, red blood cells, monocytes, lymphocytes including plasma cells, neutrophils, thrombocytes, mast cells, adipocytes, muscle cells, hepatocytes, nerve and neuroglia cells, osteocytes, and osteoblasts.

In particular embodiments, the additional tissue component is a component of the extracellular matrix. The extracellular matrix comprises diverse constituents such as glycoproteins, proteoglycans, complex carbohydrates, and other molecules. The extracellular matrix may comprise any of a number of different proteins, including various collagens, elastin, fibronectin, laminin, proteoglycans, vitronectin, thrombospondin, tenascin (cytoactin), entactin (nidogen), osteonectin (SPARC), anchorin CII, chondronectin, link protein, osteocalcin, bone sialoprotein, osteopontin, epinectin, hyaluronectin, amyloid P component, fibrillin, merosin, s-laminin, undulin, epilligrin, kalinin, fibrin, fibrinogen, and HSP.

In related embodiments, the additional tissue component comprises a growth factor, an angiogenic agent, an anti-inflammatory agent, a cytokine, or a differentiation agent. For example, a growth factor or angiogenic agent may be selected from basic fibroblast growth factor, other fibroblast growth factors, bone morphogenetic proteins, hepatocyte growth factor, keratinocyte growth factor, granulocyte macrophage colony stimulating factor, platelet-derived growth factor, transforming growth factor β1 and/or β3, vascular endothelial cell growth factor. Additional growth factors and classes or families of growth factors that may be used include any of those listed in Table 15, which also includes representative biological activities for certain growth factors.

In particular embodiments, compositions of the present invention contain no or substantially no adipose tissue, bone mineral, muscle cells, and/or blood cells, e.g., one or more of these cell types or bone mineral was removed from the composition during processing. This can increase the concentration of cells associated with the microvasculature in the composition. In particular embodiments, compositions of the present invention comprise DNA or a substantial amount of DNA, e.g., DNA was not removed from the composition during processing, for example, the tissue was not decellularized and nor was DNA washed out. In particular embodiments, a composition of the present invention is a water-soluble suspension of cells and/or tissue components. In certain embodiments, a composition of the present invention, alone, does not comprise a structural scaffold or matrix, such as, e.g., a dermal or tendon graft. In particular embodiments, a composition of the present invention may be produced using microvascular tissues such as skin, umbilical cord, or bone, which are treated to free cells from the matrix.

In particular embodiments, a composition of the present invention has one or more biological activities. For example, in certain embodiments, a composition has anti-inflammatory or angiogenic activity. In certain related embodiments, a composition promotes blood vessel formation or tissue healing. Combinations of these effects are achieved in several embodiments.

In certain embodiments, a composition of the present invention has anti-inflammatory activity. In particular embodiments, an injured or diseased tissue (e.g., an injured or diseased tissue undergoing an inflammatory response) exposed to or contacted with a composition of the present invention exhibits reduced inflammation as compared to when the injured or diseased tissue is similarly treated but not exposed to or contacted with the composition of the present invention. In certain embodiments, the amount of inflammation in the tissue exposed to or contacted with the composition of the present invention is reduced by at least about 10%, at least about 20%, at least about 30%, at least about 40%, at least about 50%, at least about 60%, at least about 70%, at least about 80%, or at least about 90%, as compared to the amount of inflammation when the injured or diseased tissue is not exposed to or contacted with the composition of the present invention. Inflammation may be measured by means available in the art, including, e.g., the number of lymphocytes observed in the affected tissue when observed histologically.

In particular embodiments, a composition of the present invention has anti-inflammatory activity that may be measured in an in vitro assay. In certain embodiments, the amount of inflammation measured in an in vitro assay in the presence of a composition of the present invention is at least about 10%, at least about 20%, at least about 30%, at least about 40%, at least about 50%, at least about 60%, at least about 70%, at least about 80%, or at least about 90% less than the amount of inflammation measured in the same assay in the absence the composition of the present invention or in the presence of a control composition. In particular embodiments, the in vitro assay is a mixed lymphocyte reaction.

In certain embodiments, a composition of the present invention has angiogenic activity. In particular embodiments, an injured or diseased tissue (e.g., an injured or diseased tissue undergoing an inflammatory response) exposed to or contacted with a composition of the present invention exhibits increased angiogenesis as compared to when the injured or diseased tissue is similarly treated but not exposed to or contacted with the composition of the present invention. In certain embodiments, the amount of angiogenesis in the tissue exposed to or contacted with the composition of the present invention is increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 300%, at least about 400%, or at least about 500%, as compared to the amount of angiogenesis when the injured or diseased tissue is not exposed to or contacted with the composition of the present invention. Angiogenesis may be measured by means available in the art, including, e.g., the hindlimb ischemia model described herein.

In particular embodiments, a composition of the present invention has angiogenic activity that may be measured in an in vivo or in vitro assay. In certain embodiments, the amount of activity measured in an in vitro angiogenesis assay in the presence of a composition of the present invention is at least about 10%, at least about 20%, at least about 30%, at least about 40%, at least about 50%, at least about 60%, at least about 70%, at least about 80%, at least 90 about %, at least about 100%, at least about 150%, at least about 200%, at least about 300%, at least about 400%, or at least about 500% greater than the amount of activity measured in the same assay in the absence the composition of the present invention or in the presence of a control composition. In particular embodiments, the in vivo assay is a matrigel assay, as described in Example 4. In particular embodiments, the in vitro assay is the endothelial cell migration assay described herein.

In certain embodiments, a composition of the present invention promotes healing of an injured or diseased tissue, i.e., it has tissue healing activity. As used herein, "tissue healing activity" of a composition is the ability of the composition to facilitate improved healing (e.g., repair or regeneration) of an injured or diseased tissue (e.g., a hard or soft tissue) exposed to the composition as compared to an analogous tissue similarly treated but without exposure to the composition. Improved healing is measured using any appropriate means, such as time to complete healing, amount of new tissue generated, strength of the resulting healed tissue, or functionality of the resulting healed tissue.

Sterilized or virus-inactivated allogeneic and xenogeneic multipotent cell and processed microvascular tissue compositions have not previously been used to facilitate repair of soft tissues such as ligaments and tendons, because of the difficulty of producing new soft tissue with autologous stem cells, the perception that allogeneic and xenogeneic stem cells will be rejected, and the prior belief that sterilized or virus-inactivated cells will have reduced viability and, thus, reduced biological or therapeutic activity. However, the process and compositions described herein do not necessarily rely on purified stem cells or cell viability. Rather, the provided process is used to produce a composition containing a mixture of cells, including nonviable cells, mesenchymal stem and progenitor cells, and other molecules secreted by such cells (e.g., cytokines, growth factors, chemotactic molecules, and the like). In some embodiments, the composition contains a mixture of viable and nonviable cells.

In particular embodiments, less than about 50%, less than about 40%, less than about 30%, less than about 20%, less than about 10%, or less than about 5% of the cells present in a composition of the present invention are viable. In several embodiments, substantially all of the cells are non-viable. As used herein, the term "viable" shall be given its ordinary meaning and shall also refer to a cell that is capable of proliferating when cultured under appropriate conditions, e.g., conditions under which the same cell or type of cell would be expected to proliferate, e.g., if not processed as described herein. In other embodiments, less than about 2% or less than about 1% of the cells present in said composition are viable. In particular embodiments, none or substantially none of the cells present in the composition are viable. Accordingly, the term "non-viable" means that the cell is not capable of proliferating when cultured under appropriate conditions, e.g., conditions under which the same cell would be expected to proliferate, e.g., if not processed as described herein.

However, in particular embodiments, at least some of the cells within a composition of the present invention exclude trypan blue. In particular embodiments, at least about 1%, at least about 2%, at least about 3%, at least about 5%, at least about 10%, at least about 20%, at least about 30%, at least about 40%, at least about 50%, at least about 60%, at least about 70%, at least about 80%, or at least about 90% of the cells present in a composition exclude trypan blue.

In certain embodiments, a composition of the present invention comprises cells that exclude trypan blue but are not viable. In certain embodiments, at least about 1%, at least about 2%, at least about 5%, at least about 10%, at least about 20%, or at least about 50% of cells present within a composition exclude trypan blue but are not viable.

It is understood according to the present invention that, although cells within the compositions described herein may not be viable and may not persist long after being transplanted into a subject, the compositions trigger a cascade of responses in the subject that lead to improved healing, reduced inflammation, or increased angiogenesis. The multipotent cell and processed microvascular tissue compositions described herein need not include viable or whole stem cells to promote or induce healing of injured or diseased tissue, such as, e.g., soft tissue. In addition, the compositions of the present invention may comprise processed tissue and various components thereof, including dissociated tissue, cells, such as multipotent cells (e.g., stem cells), cell membranes, extracellular matrix components, and various growth factors, angiogenic factors, anti-inflammatory agents, cytokines, differentiation agents, etc. present within or associated with a tissue sample used to prepare the compositions.

For the purposes of administering a composition of the invention to a subject in need thereof, the compositions may be formulated as pharmaceutical compositions. Pharmaceutical compositions of the present invention comprise a composition of the present invention and a pharmaceutically acceptable excipient, carrier and/or diluent. The composition of the invention is present in the pharmaceutical composition in an amount sufficient to effect treatment or prevention of an injury, disease or disorder in a subject in need thereof, i.e., in a therapeutically effective amount.

Pharmaceutically acceptable excipients, carriers and/or diluents are familiar to those skilled in the art. For compositions formulated as liquid solutions, acceptable carriers and/or diluents include saline and sterile water, and may optionally include antioxidants, buffers, bacteriostats and other common additives. The pharmaceutical compositions of the invention can be prepared by combining a composition of the invention with an appropriate pharmaceutically acceptable carrier, diluent or excipient, and may be formulated into preparations in solid, semi-solid, liquid or gaseous forms, such as powders, granules, solutions, injections, inhalants, microspheres and aerosols. These compositions may also contain dispersing and surface active agents, binders and lubricants. One skilled in this art may further formulate a composition of the invention in an appropriate manner, and in accordance with accepted practices, such as those disclosed in *Remington's Pharmaceutical Sciences*, Gennaro, Ed., Mack Publishing Co., Easton, Pa. 1990.

Routes of administering the pharmaceutical compositions of the invention include, without limitation, topically, intramuscular, intravenous, intraarterial, intraperitoneal, subcutaneous, oral, nasal, transplantation, implantation, injection, delivery via a catheter, topical, transdermal, inhalation, parenteral, and intranasal. The term parenteral as used herein includes subcutaneous injections, intravenous, intramuscular, intrasternal injection or infusion techniques. In addition, the compositions of the invention may be surgically implanted, injected, delivered (e.g., by way of a catheter or syringe), or otherwise administered directly or indirectly to the site in need of repair or augmentation. For example, compositions of the present invention may be surgically introduced into or adjacent to a site of injury or disease in a subject. In some embodiments, administration is intravenous. Pharmaceutical compositions may be formulated for a particular route of administration. In particular embodiments, the method is surgically for tissue repair, intravenously for treatment of ischemia, injection into joint spaces for treatment of pain and inflammation, injection into wounds, and injection into muscle for treatment of peripheral vascular disease.

In certain embodiments, a composition of the present invention is formulated for intravenous administration. A composition formulated for intravenous administration, in certain embodiments, is filtered to reduce large particles or clumps that could potentially clog capillaries or other blood vessels. In particular embodiments, a composition formulated for intravenous administration is optionally isotonic, has a pH in the range of about 5.0 to about 9.0 (e.g., about 7.3), an osmolarity between about 50 and about 600, and/or an osmolality less than or equal to about 600 mOsm/L, e.g., about 290 mOsm/L.

Implants, Matrices and Scaffolds

In certain embodiments, compositions of the present invention are combined with an implant, matrix or scaffold. Matrices may include biocompatible scaffolds, lattices, self-assembling structures and the like. Such matrices are known in the arts of cell-based therapy, surgical repair, tissue engineering, and wound healing. The matrices may be pretreated (e.g., seeded, inoculated, contacted with) with a composition of the invention. In some aspects of the invention, cells and/or tissue components present within the composition adhere to the matrix. In some embodiments, the cells are contained within or bridge interstitial spaces of the matrix. In particular embodiments, the cells and/or other tissue components are in close association with the matrix and, when used therapeutically, induce or support ingrowth of the subject's cells and/or angiogenesis.

Matrices associated with or comprising compositions of the present invention can be introduced into a subject's body in any way known in the art, including but not limited to implantation, injection, surgical attachment, transplantation with other tissue, and the like. A composition of the present invention may be combined with an implant, matrix or scaffold before being provided to or implanted within a subject, or a composition of the present invention may be combined with an implant, matrix or scaffold already present within a subject. Implants, matrices or scaffolds can provide a physical structure that retains the composition within a desired location within a subject or tissue therein, protects the composition within the subject, and/or allows release or the composition at a desired rate or over a desired time period.

The matrices used in several embodiments may be configured to the shape and/or size of a tissue or organ in vivo. The scaffolds of the invention may be flat or tubular or may comprise sections thereof, as described herein. The scaffolds of the invention may be multilayered.

In particular embodiments, the implant, matrix or scaffold is a biocompatible implant, matrix, or scaffold. The implant, matrix or scaffold may comprise a solid or liquid. The implant, matrix, or scaffold may be biodegradable. The implant, matrix or scaffold, in particular embodiments, comprises microbeads or particles, a bone-derived implant, a biofiber scaffold (e.g., BioFiber™ Scaffold), a porous resorbable polymer, a hydrogel, a putty comprising tissue product, or a suture or an implantable medical device. The implant, matrix or scaffold may be, e.g.: a collagen matrix or biocompatible fabric; an orthopedic implant; a porous, flexible implantable scaffold; a surgical implant; a porous coated implant; a polymer solution; solvents such as DMSO, N-methylpyrrolidone (NMP), and alcohols; a hydrogel; hyaluronic acid or other glycosaminoglycans or proteoglycans; collagen; fibrin; thrombin; blood clot; platelets; platelet rich plasma; demineralized bone matrix; autologous cells; and/or cancellous bone.

Compositions of the invention may be suspended in a hydrogel solution, e.g., for injection. Examples of suitable hydrogels include self-assembling peptides, such as RAD16. Alternatively, the hydrogel solution containing the cells may be allowed to harden to form a matrix having cells dispersed therein prior to implantation. The hydrogel may be an organic polymer (natural or synthetic) that is cross-linked via covalent, ionic, or hydrogen bonds to create a three-dimensional open-lattice structure that entraps water molecules to form a gel. Examples of materials that can be used to form a hydrogel include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively.

In particular embodiments, a composition of the present invention is associated with, contained within, applied to, or coating a biologically compatible implant, matrix or scaffold. In particular embodiments, a composition of the present invention is used to coat a material, such as, e.g., a flexible biocompatible scaffold (e.g., woven or nonwoven fabric sheets or thread). Spray dried processed compositions are particularly well-suited to coating a material comprising microbeads or particles without requiring reconstitution prior to coating, as coating can be done during the spray drying process. In certain embodiments, the composition is embedded within or coated on a matrix, e.g., a porous and/or collagen-containing matrix. In certain embodiments, the matrix may be Conexa™ reconstructive tissue matrix, BioFiber™ Scaffold, or BioFiber™-CM Scaffold (Tornier; Bloomington, Minn.).

In certain embodiments, compositions of the invention may be associated with a three-dimensional scaffold and implanted in vivo, where the composition induces cell proliferation on or in the framework and forms a replacement tissue in vivo. The cells that proliferate on or in the framework may include cells within the composition and/or cells of the subject in whom the scaffold is implanted. Such three-dimensional framework can be used to form tubular structures, like those of the gastrointestinal and genitourinary tracts, as well as blood vessels; tissues for hernia repair; tendons and ligaments. In related embodiments, compositions of the present invention are associated with a three-dimensional framework. The framework may be configured into the shape of the corrective structure desired.

Examples of scaffolds which may be used in the present invention include but are not limited to nonwoven mats, porous foams, or self-assembling peptides, as described, e.g., in U.S. Pat. No. 7,560,276, which is incorporated in its entirety by reference herein. Nonwoven mats may be formed using fibers comprised of a synthetic absorbable copolymer of glycolic and lactic acids (PGA/PLA) (VICRYL; Ethicon, Inc., Somerville, N.J.) or poly-4-hydroxybutyrate (PHA, Tepha, Lexington, Mass.). Foams, composed of, for example, poly(epsilon-caprolactone)/poly(glycolic acid) (PCL/PGA) copolymer, formed by processes such as freeze-drying, or lyophilized, as discussed in U.S. Pat. No. 6,355,699, may also be used. In one embodiment, the framework is a felt, which can be composed of a multifilament yarn made from a bioabsorbable material, e.g., PGA, PLA, PHA, PCL copolymers or blends, or hyaluronic acid.

Kits

The present invention further comprises kits comprising a composition, e.g., a pharmaceutical composition, of the present invention. The composition may be packaged alone, for example, in a vial, or in combination with other products, such as those suitable for combination with processed or cryopreserved microvascular tissue. When packaged with another material, the processed or cryopreserved microvascular tissue can be separately packaged, or premixed or associated with the other material. In some embodiments, processed microvascular tissue is packaged as a coating on a biocompatible material, or associated with an implant, matrix or scaffold.

In particular embodiments, a kit of the present invention comprises a moisture impermeable container comprising a composition described herein. For example, in one embodiment, a kit of the present invention comprises a moisture impermeable container comprising a sterile, dried (e.g., lyophilized) composition, wherein said composition comprises isolated multipotent cells or processed microvascular tissue, or a cell membrane comprised of said cells or tissue, wherein said cells or tissue have not been cultured, wherein said composition has angiogenic or anti-inflammatory activity, wherein said composition is sterilized and/or viruses within said composition are inactivated.

In particular embodiments of kits and compositions described herein, the composition retains measurable angiogenic or anti-inflammatory activity when stored at approximately room temperature for at least one month, at least two months, at least four months, at least six months, or at least one year. In particular embodiments of kits and compositions described herein, the composition retains measurable angiogenic or anti-inflammatory activity when stored at approximately room temperature for at least one month, at least two months, at least four months, at least six months, or at least one year. As used herein, "room temperature" is a temperature of about 20° C. to about 25° C. or about 21° C. In particular embodiments of kits and compositions described herein, the composition retains measurable angiogenic or anti-inflammatory activity when stored at approximately 4° C. for at least about one month, at least about two months, at least about four months, at least about six months, or at least about one year. In particular embodiments of kits and compositions described herein, the composition retains measurable angiogenic or anti-inflammatory activity when stored at approximately −20° C. for at least one about month, at least two about months, at least about four months, at least about six months, or at least about one year. In particular embodiments, the measurable angiogenic or anti-inflammatory activity is at least about 10%, at least about 20%, at least about 30%, at least about 40%, at least about 50%, at least about 60%, at least about 70%, at least about 80%, or at least about 90% of the activity prior to storage, when measured in an in vivo or in vitro assay, including any of those described herein.

In particular embodiments of kits and compositions of the present invention, less than or equal to 50%, less than or equal to 40%, less than or equal to 30%, less than or equal to 20%, less than or equal to 10%, or less than or equal to 5% of the cells present in said composition are viable, less than or equal to 2% of the cells present in said composition are viable, or substantially none of the cells present in said composition are viable. In related embodiments, at least 1% of said cells exclude trypan blue. In other embodiments, at least about 2%, at least about 5%, at least about 10%, at least about 20%, at least about 50%, at least about 60%, at least about 70%, at least about 80%, or at least about 90% of said cells exclude trypan blue. In certain embodiments, at least about 1%, at least about 2%, at least about 5%, at least about 10%, at least about 20%, at least about 50%, at least about 60%, at least about 70%, at least about 80%, or at least about 90% of said cells exclude trypan blue but are not viable.

According to various embodiments, a kit of the present invention may comprise a pharmaceutical composition comprising a composition of the present invention and an excipient. In one embodiment, the pharmaceutical composition is formulated for intravenous administration. In other embodiments, a kit of the present invention may comprise a composition of the present invention and an implant, scaffold or matrix, including but not limited to any of those described herein. In specific embodiments, the implantable scaffold or matrix is a bone-derived implant, a biofiber scaffold, a porous resorbable polymer, a hydrogel, a putty comprising tissue product, or a suture. In certain embodiments, cells, tissue or cell membrane of said composition are present on a bone, tendon or dermal facing surface of said implantable scaffold or matrix.

In certain embodiments, a kit of the present invention comprises a sterilized and dried (e.g., lyophilized) composition of the present invention in a sealed container. The sealed container may be moisture resistant or moisture impermeable, and it may contain a sealed opening, allowing access to the interior of the container. In certain embodiments, the container is a vial comprising a hermetic seal. In certain embodiments, the container is a blister pack, which may comprise a foil seal. In particular embodiments, the interior of the sealed container is sterile. Accordingly, prior to use, the user may access the interior of the container, add a liquid to the dried composition to dissolve or reconstitute it, and then provide or administer the reconstituted composition to a subject. In certain embodiments, the liquid is sterile water or a sterile solution such as saline, e.g., phosphate buffered saline.

Uses of the Compositions and Implants, Matrices, and Scaffolds

Compositions of the present invention, and implants, matrices, and/or scaffolds comprising said compositions, may be used to treat or prevent an injury or disease in a subject in need thereof. In various embodiments, the compositions may be provided or applied directly to a tissue in need thereof or adjacent to a tissue in need thereof, e.g., to a tissue surrounding the tissue in need thereof. Subjects in need thereof include subjects having an injury or disease, or at risk of, an injury or disease that might benefit from treatment with a composition of the present invention. In particular embodiments, a subject is a mammal, e.g., a human or other mammal, such as a non-human primate, a dog, a cat, or a horse. In certain embodiments, a subject has reduced healing capabilities, such as a diabetic subject and a subject undergoing chemotherapy.

In certain embodiments, compositions of the present invention are used to treat or prevent injury or disease of various tissues or organs in a subject, including but not limited to soft tissue injury or disease, hard tissue injury or disease, bone injury or disease, joint injury or disease, cardiac tissue injury or disease, adipose tissue injury or disease, cartilage injury or disease, and intervertebral disc injury or disease.

In certain embodiments, compositions of the present invention are used to treat or prevent a soft tissue injury. Soft tissue, as used herein, refers generally to extraskeletal structures found throughout the body and includes but is not limited to cartilage tissue, meniscal tissue, ligament tissue, tendon tissue, intervertebral disc tissue, periodontal tissue, skin tissue, vascular tissue, muscle tissue, fascia tissue, periosteal tissue, ocular tissue, pericardial tissue, lung tissue, synovial tissue, nerve tissue, brain tissue, kidney tissue, bone marrow, urogenital tissue, intestinal tissue, liver tissue, pancreas tissue, spleen tissue, adipose tissue, and combinations thereof. Soft tissue injuries include damage or injury to any soft tissue, such as, e.g., muscles, ligaments, tendons, skin, fibrous tissue, fat, synovial membranes, nerves, blood vessels, and fascia, which may occur throughout the body. Soft tissue injuries that can benefit from the soft tissue healing activity of the provided processed microvascular tissues include, without limitation, injuries such as tendon and/or ligament tears and injuries resulting from ischemic events. Common soft tissue injuries may result from sprain, strain, an injury resulting in a contusion, or overuse of a particular soft tissue. Soft tissue injuries include both open and closed soft tissue injuries.

Soft tissue injuries, disease and conditions that may be treated or prevented according to methods of the present invention include, but are not limited to, injuries to vascular, skin, or musculoskeletal tissue. Soft tissue conditions include, for example, conditions of skin (e.g., scar revision or the treatment of traumatic wounds, severe burns, skin ulcers (e.g., decubitus (pressure) ulcers, venous ulcers, and diabetic ulcers), and surgical wounds such as those associated with the excision of skin cancers); vascular condition (e.g., vascular disease such as peripheral arterial disease, coronary artery disease, abdominal aortic aneurysm, carotid disease, and venous disease; vascular injury; improper vascular development); conditions affecting vocal cords; cosmetic conditions (e.g., those involving repair, augmentation, or beautification); muscle diseases (e.g., congenital myopathies; myasthenia gravis; inflammatory, neurogenic, and myogenic muscle diseases; and muscular dystrophies such as Duchenne muscular dystrophy, Becker muscular dystrophy, myotonic dystrophy, limb-girdle-muscular dystrophy, facioscapulohumeral muscular dystrophy, congenital muscular dystrophies, oculopharyngeal muscular dystrophy, distal muscular dystrophy, and Emery-Dreifuss muscular dystrophy); conditions of connective tissues such as tendons and ligaments, including but not limited to a periodontal ligament and anterior cruciate ligament; and conditions of organs and/or fascia (e.g., the bladder, intestine, pelvic floor). One example of a fairly common soft tissue injury is damage to the pelvic floor. This is a potentially serious medical condition that may occur during childbirth or from complications thereof which can lead to damage to the vesicovaginal fascia, such as a cystocele, which is a herniation of the bladder. Similar medical conditions include rectoceles (a herniation of the rectum), enteroceles (a protrusion of the intestine through the rectovaginal or vesicovaginal pouch), and enterocystoceles (a double hernia in which both the bladder and intestine protrude).

In various embodiments, compositions of the present invention are used to treat or prevent various diseases, including but not limited to diseases associated with undesirable inflammatory or immune responses. Examples of such disease include rheumatoid arthritis, osteoarthritis, and autoimmune diseases and disorders. In addition, compositions of the present invention may be used to reduce inflammation, e.g., at a site of injury, and/or to reduce an immune response, e.g., an immune response induced by an injury. Similarly, compositions of the present invention may be used to prevent or reduce the likelihood of transplant rejection.

In particular embodiments, compositions of the present invention are used to promote or stimulate angiogenesis or revascularization, e.g., at a site of injury or tissue damage. In particular embodiments, the injury is associated with or resulted in ischemia, hypoxia, or reperfusion injury to a tissue. Examples of injuries or diseases associated with or resulting in ischemia, hypoxia, or reperfusion injury that may be treated or prevented according to the present invention include stroke, myocardial infarct, and blood loss. Additional examples of injuries or tissue damage that may be treated with compositions of the present invention to promote or stimulate angiogenesis or revascularization include transplantation or limb reattachment.

Compositions of the present invention may also be used to treat or prevent peripheral nerve damage, erectile dysfunction, pulmonary hypertension, multiple sclerosis, and radiation burns. In addition, they may be used to induce hematopoiesis and/or wound healing.

In particular embodiments, compositions of the present invention, e.g., when formulated for intravenous administration, may be used to treat or prevent acute myocardial infarct, congestive heart failure, stroke, peripheral vascular disease or chronic obstructive pulmonary disease.

The compositions of the present invention may be used alone or in combination with one or more other therapeutic agents or procedures to treat or prevent an injury or disease. For example, in certain embodiments, to enrich blood supply to a damaged tissue and/or to promote tissue regeneration, compositions of the present invention may be used in combination with platelet-rich plasma. When used in combination with one or more other therapeutic agents or procedures, the compositions of the present invention may be provided or used prior to, at the same or during an overlapping time period as, or subsequent to, treatment with the other therapeutic agent or procedure.

When used in combination with another therapeutic agent, a composition of the present invention may be provided separately from the other agent, or it may be present in a pharmaceutical composition that also contains the other therapeutic agent, e.g., a coformulation comprising two or more therapeutic agents, one being the composition of the present invention. In particular embodiments, the composition of the present invention and an additional therapeutic agent are both combined with or associated with the same implant, matrix or scaffold.

The compositions of the invention are administered in a therapeutically effective amount, which will vary depending upon a variety of factors including the activity of the specific composition employed; the age, body weight, general health, sex and diet of the subject to which the composition of the invention is administered; the mode and time of administration; the rate of excretion or breakdown of the composition in the subject; and the type or severity of the injury, disease, or condition to be treated. In certain embodiments, a therapeutically effective dose results from the material obtained by processing $10^4$ to $10^8$ multipotent cells and their associated ECM.

The methods of the present invention may be practiced by administering the composition in one, two or more doses. For example, in certain embodiments, a composition is administered as a single dose, multiple doses or in repeated doses over a period of time.

EXAMPLES

Example 1—Microvascular Tissue Preparation and Characterization

In this study, microvascular tissue is prepared via different processes and then assayed. In brief, at least 5 to 10 lbs of subcutaneous fat is obtained from an organ donor and processed as follows: mince the tissue; enzymatically dissociate it; dilute (no quench), spin, decant and then wash the cell pellet; resuspend in lyophilization buffer; and lyophilization. The base conditions used for processing are as follows: adipose tissue is surgically recovered from a tissue donor. The tissue is minced with scissors, suspended in PBS with 0.2 U/ml CIzyme AS (Vitacyte, Indianapolis, Ind.) at 37° C. with gentle agitation for 60 min, then washed three times and resuspended at two million cells/ml in M3D. The cell suspension is held at room temperature until just prior to lyophilization, when the cells are diluted 50:50 with EZ-CPZ™ cryopreservation media (Incell Corp., San Antonio, Tex.), vialed, and loaded into the lyophilizer trays for cooling. The samples are assayed both during the process and at the end of the process.

10 process methods are performed in this study. They are designated "A" through "J" in Table 1. The assay methods used to analyze each process method are listed in Table 1, designated 1, 2, 3, 4, 5, and detailed in Table 2.

TABLE 1

Process Methods, Descriptions and Assay Methods

| Process Method | Description of Process Method | *Assay Method(s) |
|---|---|---|
| A | Control: 10 gm of fat in ZTM ™ minced with scissors/scalpel immediately (<12 hr from harvest) and digested according to base conditions. | M2, 3, 4, 5 |
| B | 24 hr: 10 gm of fat in ZTM ™ stored at room temperature for 24 hr before processing with scissors/scalpel and base conditions. | M2, 4, 5 |
| C | 48 hr: 10 gm of fat in ZTM ™ stored at room temperature for 48 hr before processing with scissors/scalpel and base conditions. | M2, 4, 5 |
| D | Scale-up: 5+ pounds of fat minced using a meat grinder; digested per base conditions. | M1, 2, 3, 4 |
| E | Enzyme: 10 gm of minced fat from 'D' digested with 4X the enzyme concentration. | M2, 5 |
| F | Volume: 10 gm of minced fat from 'D' digested with 4X the enzyme concentration but in ¼ the total volume of 'E'. | M2, 5 |
| G | Lyophilization: Use formulation of 50:50 EZ-CPZ ™:M3D ™ on all of 'D' product. The shelf was cooled from room temperature to −45 C. at a cooling rate of 2.5 C./min until product temperature reached −45 C. Samples were maintained −45 C. for 180 minutes. Primary drying was initiated by raising the shelf temperature from −45 C. to −35 C. at 2.5 C./minute, reducing the chamber pressure to 80 mTorr and maintaining the shelf temperature at −35 C. for 2160 minutes. For secondary drying, samples were warmed by increasing the shelf temperature at a rate of 0.2 C./minute to 20 C. and maintaining the shelf at this temperature for 360 minutes. | M2, 3, 4, 5 |
| H | Sterilization: 2.5 Mrad of gamma radiation of 100 vials of 'G'. Use for stability. | M2, 3, 5 |
| I | Low Dose: 1.5 Mrad of gamma radiation of 80 vials of 'G'. Use for animal studies, along with 200 vials unsterilized. | M2, 3, 5 |
| J | E-Beam: 1.5 Mrad of e-beam radiation of 100 vials of 'G'. Use for stability. | M2, 3, 5 |

TABLE 2

Study Assay Groups

| Assay Group | Description |
|---|---|
| M1 | Donor screening for infectious diseases including tests not done prior to fat tissue harvest. |
| M2 | Cell counts using a hemacytometer and Trypan Blue with DAPI nuclear staining) for cell number and viability. |
| M3 | Immunophenotyping for selected Biomarkers: CD33, CD34, CD44, CD45, and collagen Type IV |
| M4 | Bioburden |
| M5 | Functional Bioassays: Cell migration; Matrigel |

Several tasks are performed for this study. They are designated A to D and described in further detail below and outlined in FIG. 1. The specific laboratory assay methods (M) used in the Tasks are designated as M1, M2, M3, M4 and M5 (Table 2).

Task A. Planning and Set-Up

Order materials, coordinate, set-up and testing.

Task B. Source Materials and General Procedures

The fat tissue is obtained from an organ donor. Subcutaneous fat is taken from abdomen, thighs and buttocks. Five (5) to ten (10) pounds of fat are harvested into ZTM™ transport medium (Incell Corp., San Antonio, Tex.).

The tissue is harvested and initially processed within 12 hours of death through various steps and laboratory methods (Tables 1 and 2; FIG. 1). Ten (10) gm aliquots are processed using base conditions after 12, 24 and 48 hours storage at room temperature. The >5+ pounds is processed using a meat grinder method for tissue mincing, and 10 gm aliquots are digested with 4× the Blendzyme I (Vitacyte) enzyme concentration in ZSolM™ and with 4× enzyme concentration and ¼ the digestion volume of ZSolM™ in Step E. The bulk of the sample is digested at the standard enzyme concentrations and methods.

After digestion, the samples are rinsed in ZSolF™, centrifuged, decanted, then washed two more spins in ZSolF™. The cells are resuspended 1:1 cell suspension in EZ-CPZ™ as a lyophilization solution bulk product at $10^6$ cells/ml and lyophilized (Step G) as 1 mL aliquot volumes. Lyophilized vials are subjected to gamma and E-beam irradiation (Steps H, I, J). All end-product is stored and representative samples are tested, and selected subsets are used in subsequent animal studies.

Task C. Assays

The various types of assays (M1 to M5) used in this study (Table 2) are briefly summarized below.

M1: Donor screening for infectious diseases including tests not done prior to fat tissue harvest. Donor screening and agreements for tissue procurement are developed to minimize or eliminate any infectious diseases according to the standard evaluations. Actual additional tests and associated costs are performed on a case-by-case basis. Bioburden assays are performed.

M2: Cell counts are performed using a hemacytometer (light microscopy) and Trypan Blue with DAPI nuclear (fluorescence microscopy) staining for cell number and viability. Cell counts are recorded as duplicate readings.

M3: Immunophenotyping for selected Biomarkers: CD33, CD34, CD44, CD45, and collagen TypeIV. Immediate immunoassays of suspended cells are performed. Cells are grown out in LabTeks then stained, and representative photos are taken.

M4: Bioburden assays are done on samples from transport solutions of received tissues in bag N=2 (and compared to post-processing {last} rinses. Endotoxin testing is performed using EndoSafe PTS Assay (Charles River). Standard USP culture microbiological testing is performed. ATP rapid testing is optionally performed.

M5: Functional bioassays are done on samples of isolated cells, post-lyophilization, and after the various processing and irradiation protocols. Cell migration assays across transwells are performed for ADSCs, endothelial, fibroblasts. Matrigel assays are performed to evaluate microvessel formation induced by samples at various dilutions, stages of processing and/or irradiation.

Task D. Data Analyses

Observational readings and data are transferred to Excel or to Prism for analysis. The mean+SD values of sample replicates for each TPS and each cell type are tabulated and/or plotted for comparative analyses.

The results obtained from preliminary experiments that were performed showed little difference between processing conditions A, B and D with 3.5 kg of adipose tissue generating 1560 vials of lyophilized product at $10^6$ cells per vial.

Example 2—Treatment of Achilles Tendon Injury in Rats

This study demonstrates that microvascular tissue preparations of the present invention can be used to repair Achilles tendon injuries.

32 male Sprague Dawley rats (8 weeks old on DAY 1 and ~250 g on DAY 1) are purchased from Harlan and acclimatized for at least 3 days. The rats are treated as summarized in the study design of Table 3.

TABLE 3

Study Design

| Group | # Animal/ group | Treatment | Route | Endpoints |
|---|---|---|---|---|
| 1 | 8 | Achilles tendon is slightly abraded with mouse-tooth forceps | Right Tibia | Surgery- implant scaffold between tibia and Achilles tendon Termination Day 7 |
| 2 | 8 | Achilles tendon is slightly abraded with mouse-tooth forceps + Tornier's Graft Material coated with Collagen | | |
| 3 | 8 | Achilles tendon is slightly abraded with mouse-tooth forceps + Tornier's Graft Material coated with Collagen + Processed microvascular tissue composition A | | |
| 4 | 8 | Achilles tendon is slightly abraded with mouse-tooth forceps + Tornier's Graft Material coated with Collagen + Processed microvascular tissue composition B | | |
| TOTAL | 32 | | | |

The study occurs over approximately 10 days of animal life. The animal arrives on day −3, is acclimatized day −3 to day 1, subjected to surgery on day 1, and scheduled for termination on day 7.

Test Articles:

Collagen Coated BioFiber Scaffolds

Processed microvascular tissue preparations A and B reconstituted with sterile WFI and absorbed into scaffolds. Processed microvascular tissue composition A is unsterilized, and processed microvascular tissue composition B is E-beam sterilized.

Anesthesia:

Prior to surgery on Day 1, animals are weighed and anesthetized with an intramuscular injection of ketamine hydrochloride 100 mg/mL (40-90 mg/kg) and xylazine 100 mg/mL (5-10 mg/kg).

Surgical Preparation:

The right rear limb of each animal is shaved one day prior to the start of the test. On Day 1, the skin is surgically prepared with betadine and alcohol scrubs, and draped using aseptic surgical techniques.

Surgical Procedure:

On Day 1, the test article is prepared immediately prior to implantation. The graft is loaded with cells by wicking action. Two 5-0 polypropylene sutures are placed in the graft for fixation. The graft is set aside in the Petri dish with saline and covered until used.

A straight, lateral skin incision is made from the caudal (distal) tibia of the right rear limb to the level of the mid tibia. Using this method, the skin is dissected and retracted to allow a lateral exposure of the Achilles tendon from calcaneus to its musculo-tendinous junction. Further dissection is used to expose and isolate the Achilles tendon. The exposed Achilles tendon is slightly abraded with mouse-tooth forceps prior to graft test article placement. A single 0.5 mm drill hole is made in the lateral to medial direction through the Calcaneus to allow suture passage for graft fixation. The implant area is irrigated with saline to remove any debris and blotted dry.

The graft is removed from the holding media and inserted along the anterior surface of the Achilles tendon with one end adjacent to the calcaneus. The cranial graft fixation suture is placed in the gastrocnemius cranial to the musculo-tendinous junction using a modified Mason-Allen suture pattern. The caudal graft fixation suture is then passed through the drill hole in the calcaneus and tensioned with the foot in a neutral position and tied. Six suture knots are tied for all fixation sutures. The incision is closed in a layered fashion using appropriate suture material.

Analgesia:

Animals are administered buprenorphine (0.1-0.5 mg/kg) subcutaneously upon recovery from anesthesia on Day 1. Additional buprenorphine may be administered discretionarily as needed for pain.

Body Weight Measurement:

Animals are weighed at randomization, prior to surgery on Day 1, and once a week until end of study, including prior to termination. (~9 time points)

Health Observations:

Animals are monitored once daily for the duration of the study. (~7 time points)

Incision Site Area Observations:

Observations of the incision site are recorded daily from Day 2 through Day 7.

Temperature/Humidity Recordings:

Daily room temperature and humidity measurements are recorded.

Termination and Tissue Collection:

On Day 7, animals are euthanized and the implanted test or control article sites and surrounding tendinous tissue are collected by excision from each animal. All collected samples are split in half along the mid-line of the scaffold with half the tendon included in each half. One-half of the collected tissue is stored in 10% neutral buffered formalin for routine histopathological and immunohistochemistry evaluation. The remaining half is stripped of tendon and overgrown soft tissue with the edge of a scalpel, and the scaffold with ingrown tissue is snap frozen at $\leq-70°$ C. in liquid nitrogen for gene expression analysis.

Sections of tendon (taken from the contralateral Achilles), skin (taken from a region with less fur) and liver of 2 animals/group randomly selected are also collected as staining controls and stored in 10% neutral buffered formalin for immunohistochemistry evaluation. A portion of each control tissue is snap frozen in liquid nitrogen for PCR controls. (All three control tissues can be stored together in formalin and the frozen portions can likewise be stored together).

The tissues are subjected to histology (H&E, Masson's trichrome), immunohistochemistry (SMAD8 and tenascin), and PCR (SMAD8, tenascin, tenomodulin, and scleraxis) analysis.

Example 3—Treatment of Ischemia in Mice

This study demonstrates the effects of processed microvascular tissue compositions of the present invention in a murine model of limb ischemia. The murine model of limb ischemia is created as previously described (Jang J et al, Circulation 1999; Huang N et al, JOVE 2009), and is used to assess the effects of cell preparations in promoting angiogenesis after induction of hindlimb ischemia.

SCID mice 14-16 weeks old undergo surgically induced hindlimb ischemia. Immediately after surgery, processed microvascular tissue composition or vehicle control will be administered to the animals as detailed in Table 4 below. Briefly, three test cell articles (each at $0.5 \times 10^6$ cells) or vehicle control are injected intramuscularly on day 0 after induction of hindlimb ischemia into the gastrocnemius. The three test articles include: processed microvascular tissue composition (Test Cells-I), processed microvascular tissue composition sterilized by E-beam (Test Cells-II), and processed microvascular tissue composition sterilized by gamma radiation (Test Cells-III). Improvement in limb perfusion is evaluated every 3-4 days for a total of 14 days. After 14 days, the animals are euthanized. Both the ischemic and contralateral gastrocnemius are explanted and subjected to histological analysis.

TABLE 4

Study Protocol

| Group | # animals | Test Material |
|---|---|---|
| 1 | 10 | Vehicle |
| 2 | 10 | Test Cells- I ($0.5 \times 10^6$) |
| 3 | 10 | Test Cells- II ($0.5 \times 10^6$) |
| 4 | 10 | Test Cells- III ($0.5 \times 10^6$) |

Endpoint Testing

Bloodflow is evaluated by Laser Doppler Imaging at Days 0, 3, 7, 11 and 14.

Animals are sacrificed at Day 14, and hindlimb tissue is harvested, processed and stored for explant studies.

Example 4—Vessel Formation in SCID Mice

These studies utilize matrigel plug assays to demonstrate the ability of the microvascular tissue preparations of the present invention to form vascular structures in vivo. The matrigel plug assay is a definitive assay of true vessel formation in vivo. This assay involves implantation of therapeutic cells with matrigel subcutaneously into the abdominal region. During the course of 2 weeks, the cells within the matrigel are in a favorable environment to form neovessels, some of which may anastamose with host vessels.

In this assay, $0.5 \times 10^6$ cells are embedded in 0.5 ml matrigel supplemented with 200 ng/ml basic fibroblast growth factor and then injected subcutaneously into SCID mice. 2 plugs are implanted into each animal. After 2 weeks, the plugs are explanted for histological analysis of vessel formation. To distinguish human from native murine vessels, human specific antibodies targeting endothelial cells (e.g., CD31) are used to identify human-specific vessels. The presence of human specific vessels, as demonstrated histologically by luminal structures performed with blood elements, is demonstrative of functional endothelial cells. Similarly, mouse-specific endothelial cell antibodies can be used to identify mouse-specific vessels. The ability of therapeutic cells to secrete paracrine angiogenic factors results in a relative enhancement in murine vessel formation.

SCID mice 14-16 weeks old undergo implantation of matrigel plugs containing microvascular tissue preparations of the present invention or vehicle control, as detailed in Table 5 below.

TABLE 5

Study Protocol

| Group | # animals | Test Material |
|---|---|---|
| 1 | 5 | Vehicle |
| 2 | 5 | Test Cells- I ($0.5 \times 10^6$) |
| 3 | 5 | Test Cells- II ($0.5 \times 10^6$) |
| 4 | 5 | Test Cells- III ($0.5 \times 10^6$) |

The three test articles include: processed microvascular tissue composition (Test Cells-I), processed microvascular tissue composition sterilized by E-beam (Test Cells-II), and processed microvascular tissue composition sterilized by gamma radiation (Test Cells-III).

Example 5—Treatment of Rheumatoid Arthritis in Rats

This study demonstrates the efficacy of microvascular tissue preparations of the present invention in inhibiting the inflammation, cartilage destruction and bone resorption associated with 7 day established type II collagen arthritis in rats.

Test System

Number of animals: 44

Species/Strain or Breed: Lewis rats

Vendor: Charles River

Age/Wt at Arrival: 125-150 g

Gender: Female

Age Range at Study Initiation: At least 125 grams at time of first immunization.
Acclimation: Acclimated for 4-8 days after arrival at BBP.
Housing: 3-5/animals/cage
Materials
Test articles (Processed microvascular tissue composition preparations) and appropriate vehicle. Triamcinolone and sterile saline for dilution (BBP), Bovine Type II collagen (Elastin Products), Freund's incomplete adjuvant (Difco).

General Study Design

Rats are anesthetized with Isoflurane and given 300 µl of Bovine Type II collagen in Freund's incomplete adjuvant injections ID/SC spread over the distal back, 100 µls per site on Day 0 and again on day 6.

Randomization into each group occurs on day 1 of arthritis (study day 10) when disease is obvious in both hind paws (knees will generally have disease of similar severity to ankles but are difficult to reliably caliper so the ankle measure is a surrogate for the knee for purposes of determining disease onset). This becomes day 1 of arthritis. Animals with arthritis are randomized into treatment groups with approximate mean ankle caliper measures for each group.

Treatment (IA, bilateral into both knees) occurs on arthritis day 1 only. Knees are treated, because ankles are too small to inject. Systemic effects of treatment are monitored by caliper measures of ankles and local effects of treatment are determined by histopathology on the knees. Ankle caliper measures are taken daily from days 0 (baseline)-7. Baseline ankle caliper measurements are taken on day 0 using one ankle with values rounded to one-thousandth of an inch. Measurements are confirmed as clinically normal (0.260-0.264 in) by comparison with historical values for rats based on a range of body weights. Baseline measurements are then applied to both ankles, and these values remain with the animal so long as the ankle is clinically normal with good definition of all the ankle bones and no evidence of inflammation.

composition sterilized by E-beam (TX-II), and processed microvascular tissue composition sterilized by gamma radiation (TX-III).

Disease Induction

Acclimated animals areanesthetized with Isoflurane and given collagen injections (D0). On day 6, they are anesthetized again for the second collagen injection. Collagen is prepared by making a 4 mg/ml solution in 0.01N Acetic acid. Equal volumes of collagen and Freund's incomplete adjuvant are emulsified by hand mixing until a bead of this material holds its form when placed in water. Each animal gets 300 µl of the mixture each time spread over 3 subcutaneous sites (100 µl per site) on back.

Materials

Name (Vendor): Type II Collagen (Elastin Products)

Designation: Bovine Type II Collagen

Characteristics: Soluble, from new born calf joints

Storage Conditions: 2-8° C.

Purity: >99.6%

Name (Vendor): Freund's Incomplete adjuvant (Difco)

Designation: Incomplete Adjuvant

Storage Conditions: 2-8° C.

Test Article and Vehicle

Test Article Vehicle: Stem cell preparations prepared on the day of injection, Triamcinolone (Vetalog, Ft. Dodge).

Test Article and Formulation: Stem cell preparations in physiologic vehicle at concentrations appropriate for inject-

TABLE 6

Study Group Designations

| Group | N | Compound | Route | Regimen | Dose Level | Dose Vol | Dose Conc |
|---|---|---|---|---|---|---|---|
| Grp 1 | 4 | Naïve | N/A | N/A | N/A | N/A | N/A |
| Grp 2 | | Vehicle Control | IA | Bilateral, D1 | | 40 µl | |
| Grp 3 | 8 | Triamcinolone | IA | Bilateral, D1 | 0.03 mgs | 40 µl | 0.75 mg/ml |
| Grp 4 | 8 | TX-1 | PO | Bilateral, D1 | $2 \times 10^5$ cells | 40 µl | $5 \times 10^6$ cells/ml |
| Grp 5 | 8 | TX-2 | PO | Bilateral, D1 | $2 \times 10^5$ cells | 40 µl | $5 \times 10^6$ cells/ml |
| Grp 6 | 8 | TX-3 | PO | Bilateral, D1 | $2 \times 10^5$ cells | 40 µl | $5 \times 10^6$ cells/ml |

The three test articles include: processed microvascular tissue composition (TX-I), processed microvascular tissue ing 40 µl/knee joint. Triamcinolone 2 mg/ml to be diluted in saline.

TABLE 7

Study Calendar

| Day −8 | | | | | |
|---|---|---|---|---|---|
| Distribute rats on arrival into groups for acclimation | | | | | |
| | Day 0 | Day 1 | Day 2 | Day 3 | Day 4 |
| | Anesthetize, 1st Collagen Injection | | | | |

TABLE 7-continued

| Study Calendar | | | | | | |
|---|---|---|---|---|---|---|
| Day 5 | Day 6 | Day 7 | Day 8 | Day 9 (0) | Day 10 (1) | Day 11 (2) |
| | 2nd Collagen Injection | | | Weigh, Caliper Baseline | Weigh, Dose, Caliper (Enroll) | Weigh, Caliper |
| X/XX/2012 Day 12 (3) | X/XX/2012 Day 13 (4) | X/XX/2012 Day 14 (5) | X/XX/2012 Day 15 (6) | X/XX/2012 Day 16 (7) | X/XX/2012 Day 17 | X/XX/2012 Day 18 |
| Weigh, Caliper | Weigh, Caliper | Weigh, Caliper | Weigh, Caliper | Weigh, Caliper Necropsy | | |

Live Phase Conduct

Randomization into each group by arthritis severity is done on arthritis day 1 (study day 10). Treatment (bilateral IA, 40 µl/joint) is initiated after randomization (day 1). Body weights and ankle caliper measures/scores are taken daily.

Humane Practice: Animals showing signs of morbidity according to the Bolder BioPATH IACUC Program of Veterinary Care, including the loss of more than 20% body weight (within one week) are removed from the study and humanly sacrificed via $CO_2$ inhalation.

TABLE 8

| Live Phase Deliverables | | |
|---|---|---|
| Live Phase Data Collection: | | |
| Body Weight | Arthritis days 0-7 | |
| Caliper Measure | Arthritis days 0-7 | Left & Right Ankles |
| Live Phase (Non PK) Sample Collection | | |
| N/A | N/A | N/A |

Necropsy

Animals are sacrificed on Arthritis Day 7 by exsanguination.

Necropsy data is collected, including the weight of both the left and right hind paws, and the weight of the liver, spleen and thymus.

Necropsy samples collected include an aliquot of term serum, and the left and right hind paws and kneed.

Processing of Joints/Histopathologic Scoring

Following 1-2 days in fixative and then 4-5 days in decalcifier, the ankle joints are cut in half longitudinally, knees are cut in half in the frontal plane, processed, embedded, sectioned and stained with toluidine blue.

Histopathologic Scoring Methods for Rats Joints with Type II Collagen Arthritis

Collagen arthritic ankles and knees are given scores of 0-5 for inflammation, pannus formation and bone resorption according to the following criteria:

Knee and/or Ankle Inflammation
  0=Normal
  0.5=Minimal focal inflammation
  1=Minimal infiltration of inflammatory cells in synovium/periarticular tissue.
  2=Mild infiltration
  3=Moderate infiltration with moderate edema.
  4=Marked infiltration with marked edema
  5=Severe infiltration with severe edema The inflammatory infiltrate in mice and rats with type II collagen arthritis consists of neutrophils and macrophages with smaller numbers of lymphocytes when the lesions are in the acute to subacute phase. Tissue edema and neutrophil exudates within the joint space are common in the acute to subacute phase. As the inflammation progresses to chronic, mononuclear inflammatory cells (monocytes, lymphocytes) predominate and fibroblast proliferation, often with deposition of metachromatic matrix, occurs in synovium and periarticular tissue. Exudate is less common in the joint space. Unless indicated in the comments area, the inflammation type is acute to subacute.

Ankle Pannus
  0=Normal
  0.5=Minimal infiltration of pannus in cartilage and subchondral bone, affects only marginal zones and only a few joints.
  1=Minimal infiltration of pannus in cartilage and subchondral bone, primarily affects marginal zones.
  2=Mild infiltration (<¼ of tibia or tarsals at marginal zones)
  3=Moderate infiltration (¼ to ⅓ of tibia or small tarsals affected at marginal zones)
  4=Marked infiltration (½-¾ of tibia or tarsals affected at marginal zones)
  5=Severe infiltration (>¾ of tibia or tarsals affected at marginal zones, severe distortion of overall architecture)

Knee Pannus
  0=Normal
  0.5=Minimal infiltration of pannus in cartilage and subchondral bone, affects only marginal zones and only a few joints.
  1=Minimal infiltration of pannus in cartilage and subchondral bone, approximately 1-10% of cartilage surface or subchondral bone affected.
  2=Mild infiltration (extends over up to ¼ of surface or subchondral area of tibia or femur), approximately 11-25% of cartilage surface or subchondral bone affected
  3=Moderate infiltration (extends over >¼ but <½ of surface or subchondral area of tibia or femur) approximately 26-50%/o of cartilage surface or subchondral bone affected
  4=Marked infiltration (extends over ½ to ¾ of tibial or femoral surface) approximately 51-75% of cartilage surface or subchondral bone affected
  5=Severe infiltration approximately 76-100% of cartilage surface or subchondral bone affected Ankle Cartilage Damage (Emphasis on Small Tarsals)
  0=Normal
  0.5=Minimal decrease in T blue staining, affects only marginal zones and affects only a few joints 1=Minimal to mild loss of toluidine blue staining with no obvious chondrocyte loss or collagen disruption
2=Mild loss of toluidine blue staining with focal mild (superficial) chondrocyte loss and/or collagen disruption
3=Moderate loss of toluidine blue staining with multifocal moderate (depth to middle zone) chondrocyte loss and/or collagen disruption, smaller tarsals affected to ½-¾ depth with rare areas of full thickness loss
4=Marked loss of toluidine blue staining with multifocal marked (depth to deep zone) chondrocyte loss and/or collagen disruption, 1 or 2 small tarsals surfaces have full thickness loss of cartilage
5=Severe diffuse loss of toluidine blue staining with multifocal severe (depth to tide mark) chondrocyte loss and/or collagen disruption affecting more than 2 cartilage surfaces Knee Cartilage Damage
0=Normal
0.5=Minimal decrease in T blue staining, affects only marginal zones
1=Minimal to mild loss of toluidine blue staining with no obvious chondrocyte loss or collagen disruption
2=Mild loss of toluidine blue staining with focal mild (superficial) chondrocyte loss and/or collagen disruption, may have few small areas of 50% depth of cartilage affected
3=Moderate loss of toluidine blue staining with multifocal to diffuse moderate (depth to middle zone) chondrocyte loss and/or collagen disruption, may have 1-2 small areas of full thickness loss affecting less than ¼ of the total width of a surface and not more than 25% of the total width of all surfaces
4=Marked loss of toluidine blue staining with multifocal to diffuse marked (depth to deep zone) chondrocyte loss and/or collagen disruption or 1 surface with near total loss and partial loss on others, total overall loss less than 50% of width of all surfaces combined
5=Severe diffuse loss of toluidine blue staining with multifocal severe (depth to tide mark) chondrocyte loss and/or collagen disruption on both femurs and/or tibias, total overall loss greater than 50% of width of all surfaces combined Ankle Bone Resorption
0=Normal
0.5=Minimal resorption affects only marginal zones and affects only a few joints
1=Small areas of resorption, not readily apparent on low magnification, rare osteoclasts
2=Mild-more numerous areas of resorption, not readily apparent on low magnification, osteoclasts more numerous, <¼ of tibia or tarsals at marginal zones resorbed
3=Moderate=obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones
4=Marked=Full thickness defects in cortical bone, often with distortion of profile of remaining cortical surface, marked loss of medullary bone, numerous osteoclasts, ½-¾ of tibia or tarsals affected at marginal zones
5=Severe-Full thickness defects in cortical bone, often with distortion of profile of remaining cortical surface, marked loss of medullary bone, numerous osteoclasts, >¾ of tibia or tarsals affected at marginal zones, severe distortion of overall architecture Knee Bone Resorption
0=Normal
0.5=Minimal resorption affects only marginal zones
1=Minimal=small areas of resorption, not readily apparent on low magnification, approximately 1-10% of total joint width of subchondral bone affected
2=Mild-more numerous areas of resorption, definite loss of subchondral bone, approximately 11-25% of total joint width of subchondral bone affected
3=Moderate-obvious resorption of subchondral bone approximately 26-50% of total joint width of subchondral bone affected
4=Marked=obvious resorption of subchondral bone approximately 51-75% of total joint width of subchondral bone affected
5=Severe=distortion of entire joint due to destruction approximately 76-100% of total joint width of subchondral bone affected Periarticular Matrix Deposition (Only Scored if an Increase is Seen in any Treated Group Relative to Disease Controls)
0=Normal
1=Faint, multi-focal metachromatic staining, no excessive expansion of periarticular tissue
2=Darker, diffuse metachromatic staining, no excessive expansion of periarticular tissue
3=Darker, diffuse metachromatic staining, mild expansion of periarticular tissue
4=Darker, diffuse metachromatic staining, moderate expansion of periarticular tissue
5=Darker, diffuse metachromatic staining, severe expansion of periarticular tissue Statistical Analysis
Clinical Data Data are analyzed using a Student's t-test or Mann-Whitney U test (non-parametric). If applicable, data are further analyzed across all groups using a one-way analysis of variance (1-way ANOVA) or Kruskal-Wallis test (non-parametric), along with the appropriate multiple comparison post-test. Unless indicated, statistical analysis is performed on raw (untransformed) data only. Statistical tests make certain assumptions regarding the data's normality and homogeneity of variance, and further analysis may be required if testing resulted in violations of these assumptions. Significance for all tests is set at $p \le 0.05$.

Percent inhibition of paw weight and AUC is calculated using the following formula:

$$\% \text{ Inhibition} = A - B/A \times 100$$

A=Mean Disease Control−Mean Normal
B=Mean Treated−Mean Normal

Example 6—Treatment of Bone Voids, Cartilage Defects and Meniscal Lesions in Goats This study demonstrates the effect of the microvascular tissue preparation of the present invention in the treating bone voids, cartilage defects and meniscal lesions. In this study, for each animal, the right rear stifle joint is operated on, and 3 distinct and separate surgical defects are created. Each right femur tested will have one 8 mm diameter by 20 mm deep bone defect made in the lateral epicondylar region of the femur, one 4×7 mm rectangular by 2 mm deep cartilage defect created in the trochlear sulcus, and one 7 mm long by 1-2 mm wide full thickness meniscal defect created in the white-white zone of the medial meniscus. The treatment group of 3 animals has each defect treated with the microvascular tissue preparation, while the control group has the defects filled with just the scaffold. The goats are evaluated at 8 weeks to evaluate and characterize the repaired tissue in the various defect sites. It is expected that the treated defects will be superior in gross and histologic appearance compared to the controls.

The goat was chosen because of the large relative stifle joint size, ease of handling, use in other cartilage, meniscal and bone repair studies, and similarity of response to that seen in the human. Various species of goats have been used for cartilage research due to their large joint size, similarity of meniscal repair physiology, thickness of cartilage in the knee (Stifle) joint between 1.5-2 mm, similar to horses and humans, and that they possess cancellous and cortical bone similar to humans (secondary osteonal). The bone, cartilage and meniscal repair processes are a very complex process which cannot be mimicked in an in vitro setting. Animal models are necessary as the physiology of joints, especially injured joints, is very complex and cannot be duplicated in the laboratory. The animals used in this study are summarized in Table 9.

TABLE 9

Animal Use

| Common Name | Number | Age | Weight | Sex | # Housed Simultaneously | Housing Duration |
|---|---|---|---|---|---|---|
| Nubian Boer-Cross Goat | 6 | 2-4 yo | >120 lb. | Castrated Male | 6 | 6 @ 12 weeks |
| Nubian Boer-Cross Goat | 2 | 2-4 yo | >120 lb. | Castrated Male | 2 | Replacement animals; maximum of 12 weeks |

One unicortical epicondylar 8 mm diameter by 20 mm deep defect is created in the lateral epicondylar region of the right femur; one 4×7 mm by approximately 2 mm deep rectangular defect is created in the lateral trochlear sulcus of the right femur, and one approximate 7 mm long by 1-2 mm wide full thickness defect will be created in the right medial meniscus. Each knee is physically examined for drawer, range of motion (goniometer), swelling, temperature, crepitus, patella tracking, and valgus/varus. A standard surgical scrub with chlorohexidine followed by 70% alcohol and followed with a paint of betadine is performed. The surgical approach consists of a curved, medial skin incision made from the distal one-third of the right femur to the level of the tibial plateau.

The medial collateral ligament is identified and an outline of the bone-ligament attachment footprint is made with cautery. In the center of the footprint, a 2.8 mm drill bit and tap is used to create a screw hole for reattachment of the ligament. An oscillating saw is used to cut the attachment footprint of the medial collateral ligament, allowing for it to be reflected towards the tibia. The joint capsule is opened, and the knee is flexed and rotated laterally to expose the medial meniscus. A plastic protective tab is placed under the medial meniscus and using a specially designed oval punch, a full thickness defect is made in the white-white zone of the meniscus. The defect is then either treated with scaffold or scaffold+compound. The knee is straightened and the medial collateral ligament is reattached with a screw and washer.

The knee is then flexed, and the mid-point of the lateral trochlea sulcus is identified. The point of drilling for the cartilage defect is defined as 20 mm distal to the proximal border of the lateral trochlear groove. The cartilage is scored with a 6 mm diameter punch, and using specialized instruments, a 6 mm diameter by approximate 2 mm deep defect is made in the cartilage surface. This defect is then either treated with scaffold or scaffold+compound.

With the knee still flexed, a collared 3 mm diameter bit is used to drill a pilot hole in the epicondylar region of the lateral femoral condyle to a depth of 20 mm. The drill bit is aligned perpendicular to the joint line and parallel to the anterior surface. This pilot hole is then enlarged to a diameter of 8 mm. The bone defect is flushed and then either treated with a scaffold or scaffold+compound.

Following closure of the surgical incision in 3 layers using 1-0 Vicryl for the deep layers and skin staples, a modified Thomas splint is applied to the leg to limit weight bearing and motion. The fiberglass cast and splint will remain on for a minimum of 14+2 days post-operatively. During this time animals will be maintained in small paddocks.

TABLE 10

Treatment assignment per defect

| Group | Number of Animals | Treatment |
|---|---|---|
| 1 | 1 | Bone Defect: Compound<br>Cartilage Defect: Compound<br>Meniscal Defect: Compound |
| 1 | 2 | Bone Defect: Compound<br>Cartilage Defect: Compound<br>Meniscal Defect: Compound |
| 1 | 3 | Bone Defect: Compound<br>Cartilage Defect: Compound<br>Meniscal Defect: Compound |
| 1 | 4 | Bone Defect: Scaffold<br>Cartilage Defect: Scaffold<br>Meniscal Defect: Scaffold |
| 2 | 5 | Bone Defect: Scaffold<br>Cartilage Defect: Scaffold<br>Meniscal Defect: Scaffold |
| 2 | 6 | Bone Defect: Scaffold<br>Cartilage Defect: Scaffold<br>Meniscal Defect: Scaffold |

Animals are euthanized under stage III anesthesia with Potassium Chloride IV at days 84+2, postoperatively. Following euthanasia, the stifle joints are grossly evaluated, synovial fluid evaluated grossly for color and viscosity, and samples collected as described in Table 12. The joints will be opened, photographed and the surface of the chondral sites scored as indicated in Table 13. The articulating surfaces opposing the defect sites will be examined for any abnormal joint surface. Gross evaluation will be performed on the control and operated knee joints. Popliteal lymph nodes and the synovial membranes will be examined for any inflammation.

TABLE 11

Gross Evaluation and Sample Collection

| Sample | Gross Evaluation | Photograph and Score | Sample collection |
|---|---|---|---|
| Right Popliteal lymph node | X | | |
| Right Knee Joint cartilage and meniscus | X | X | X(H) |
| Left Popliteal lymph node | X | | |
| Left Knee Joint cartilage and meniscus | X | X | |

H = histology - Only right femur: bone defect, trochlear defect, medial meniscus The contralateral knee is examined for any abnormal joint surface. Gross morphological evaluations of the right knee joints are made to determine the chondral surface repair based on previous scoring criteria listed in Table 3. The right femora is cut to separate the cartilage defect from the bone void region and placed into appropriately labeled containers filled with a 10-fold volume of 10 percent neutral buffered formalin. The medial meniscus is evaluated grossly, harvested and placed into appropriately labeled containers filled with a 10-fold volume of 10 percent neutral buffered formalin.

TABLE 12

Scoring Criteria for Gross Morphological Evaluations

| Characteristic | Grading | Score |
| --- | --- | --- |
| Edge Integration (new tissue relative to native cartilage) | Full | 2 |
| | Partial | 1 |
| | None | 0 |
| Smoothness of the cartilage surface | Smooth | 2 |
| | Intermediate | 1 |
| | Rough | 0 |
| Cartilage surface, degree of filling | Flush | 2 |
| | Slight depression | 1 |
| | Depressed/overgrown | 0 |
| Color of cartilage, opacity or translucency of the neocartilage | Opaque | 2 |
| | Translucent | 1 |
| | Transparent | 0 |

Synovial fluid is collected, evaluated for volume, viscosity (string), clarity and color. As appropriate, a semi-quantitative scoring of the gross synovial fluid evaluation is applied as outlined in Table 13.

TABLE 13

Description and Score for Synovial Fluid

| Score | Color | Clarity | String |
| --- | --- | --- | --- |
| 0 | S = STRAW | C = CLEAR | N = NORMAL |
| 1 | P = PINK | H = HAZY | A = ABNORMAL |
| 2 | Y = YELLOW/R = RED | D = CLOUDY | W = WATERY |
| 3 | B = BLOODY | T = TURBID | |

Total synovial fluid score is a sum of the color, clarity and string scores (0-8 points).

Example 7—Cell Migration Assays Using Processed Rat Microvascular Tissue

To demonstrate the effect of the processed microvascular tissue composition on cell migration, assays of human endothelial cell migration (chemoattraction by processed microvascular tissue compositions) and labeled processed microvascular tissue composition microvesicle (MV) uptake by adipose-derived stromal vascular fraction (SVF) cells were developed and used as measures of the composition's biological activity.

The rationale for choosing these studies was that: (1) the processed microvascular tissue composition may induce increases in vascular repair; thus, endothelial cell migration would be a valid metric; and (2) MV release and uptake is an important activity that would occur in multiple cell types in a tissue repair model; thus, the SVF cell population, which has cell types important for vascular repair was used to test MV uptake.

General Study Design

To assay chemoattraction ability of the processed microvascular tissue composition for endothelial cells, samples of the composition were placed into the bottom chambers of transwell plates, and migration of endothelial cells labeled with an orange-red fluorescent lipophilic dye (CM-DiI) was monitored over time, from 12 to 48 hr. The assay also included a chemically defined cryopreservation medium EZ-CPZ™ (Incell Corp., San Antonio, Tex.) at 100% and as a 50/50 mix of EZ-CPZ™ with M3D™ (Incell Corp., San Antonio, Tex.) media as a baseline control.

A second study was performed to assess uptake of the lyophilized processed microvascular tissue composition by SVF cells. The composition was incubated with CM-DiI to allow the dye to be incorporated into the MVs and cell membranes of the composition samples. The labeled composition samples were rinsed, diluted in media, then placed onto attached monolayer cultures of SVF cells. After 24 hr uptake the cells were rinsed, then visualized for uptake of red fluorescent dye.

Materials and Methods

M3D™ is a chemically defined culture medium manufactured by INCELL. In some assays M3D™ was supplemented with antibiotics (1×PSF: Pen/Strep/Fungizone antibiotic/antimycotic; Invitrogen, Grand Island N.Y.). M3D:10 medium (INCELL) was M3D™ supplemented with 10% fetal bovine serum (FBS) and 1×PSF. EZ-CPZ™ (Incell Corp., San Antonio, Tex.) is a chemically defined cell cryopreservation medium. EZ-CPZ™ and EZ-CPZ™: M3D™ (1:1; v/v) were used as reference control media.

CM-DiI is the "Cell Tracker®" fluorescent dye in an aqueous formulation for culture medium (Invitrogen/Molecular Probes). It becomes associated with lipophilic materials such as cell membranes and MVs and can be visualized as bright red fluorescence by fluorescence microscopy. For this study, an EVOS inverted microscope was used with a red filter: 530 nm excitation, 593 nm emission).

Human umbilical vein endothelial cells (HUVEC) at passage 1 (p1) were retrieved from the INCELL Bioreposity. Human SVF p1 cells for the MV uptake assays were retrieved from the INCELL Biorepository.

All cells were grown in M3D:10™ (Incell, San Antonio, Tex.). Endothelial cells were incubated with CM-DiI for 30 minutes at 37° C. and then rinsed with M3D™ with 1×PSF. Cells were counted and an equal number of cells per well was applied to the top chamber of 3 micron pore size PET transwell chambers (Thermofisher; Waltham, Mass.) pre-loaded with the processed microvascular tissue composition test materials in triplicate wells.

The SVF cells for the adsorption assay were grown in 48-well plates into log phase growth.

Processed Microvascular Tissue Composition

Two processed microvascular tissue compositions were prepared and tested, i.e., BMA and BMB. BMA samples were rat SVF cells, and BMB were rat bone marrow mononuclear cells each lyophilized at $10^6$ cells/ml. The rat SVF cells were prepared by mincing epididymal fat pads with scissors until no pieces were larger than 1 mm in diameter then washed and incubated in 1 U/ml CIzyme AS (Vitacyte, Indianapolis, Ind.) in PBS for 60 min at 37 C with gentle agitation. The cells were washed twice and resuspended at $10^6$/ml in lyophilization buffers. Rat bone marrow cells were obtained by flushing the femurs and tibias with ACDA/PBS solution and dissociated by repeated aspiration and expulsion through a 20 ga needle. The bone marrow cells were then separated on a Ficoll gradient, washed with PBS+1% FBS twice and resuspended in buffers. Following lyophilization, the BMA samples gave cell counts below the detection limit (under 10,000), while the BMB samples gave cell counts of 0.6 to 1.0 million and

TABLE 14

Viability of BMA and BMB Preparations

| Samples | # Cells Pre-lyoph | Post-lyoph | Viability (%) | #Vials |
|---|---|---|---|---|
| BMA Buffer 1 | 45,000 | 2,500 | 80 | 3 |
| BMA Buffer 2 | 27,000 | 7,500 | 0 | 3 |
| BMA Buffer 1 | $4.4 \times 10^5$ | $6 \times 10^5$ | 48 | 4 |
| BMA Buffer 2 | $5 \times 10^5$ | $10 \times 10^5$ | 10 | 4 |

All samples were stored refrigerated in the dark for a year, and test samples were sterilized with 11 kGy E-beam radiation. Non-irradiated control samples were not sterilized.

Transwell Migration of Labeled Endothelial Cells

The lyophilized material was reconstituted in 1 ml of UFDI water with 1×PSF. Of this total sample, 300 µl was placed in the bottom of each of 3 wells and brought to a final volume of 500 µl with 200 µl M3D. The upper chambers were set into the sample wells, and an equal number of CM-DiI labeled HUVEC p2 cells was placed in each one. The plate was incubated at 37° C., and wells were imaged at 12, 24 and 48 hours. The images were examined by counting cells in fields to determine the results.

Uptake of Labeled Microvesicles by SVF Cells

The remaining 100 µl of lyophilized material was incubated with CM-DiI to label the cell membranes present. The material was washed 3 times with M3D+1×PSF by centrifugation. SVF cells seeded onto 48-well plates for the absorption assay were grown to 50% confluence and had 50 µl CM-DiI labeled lyophilized material layered on top. Half of the wells were rinsed at 24 hours, coated with liquid mount and allowed to dry, the other half was rinsed, fixed and mounted after 3 days. The images were examined to determine the results.

Results

Transwell Migration of Labeled Endothelial Cells

Figure 2:
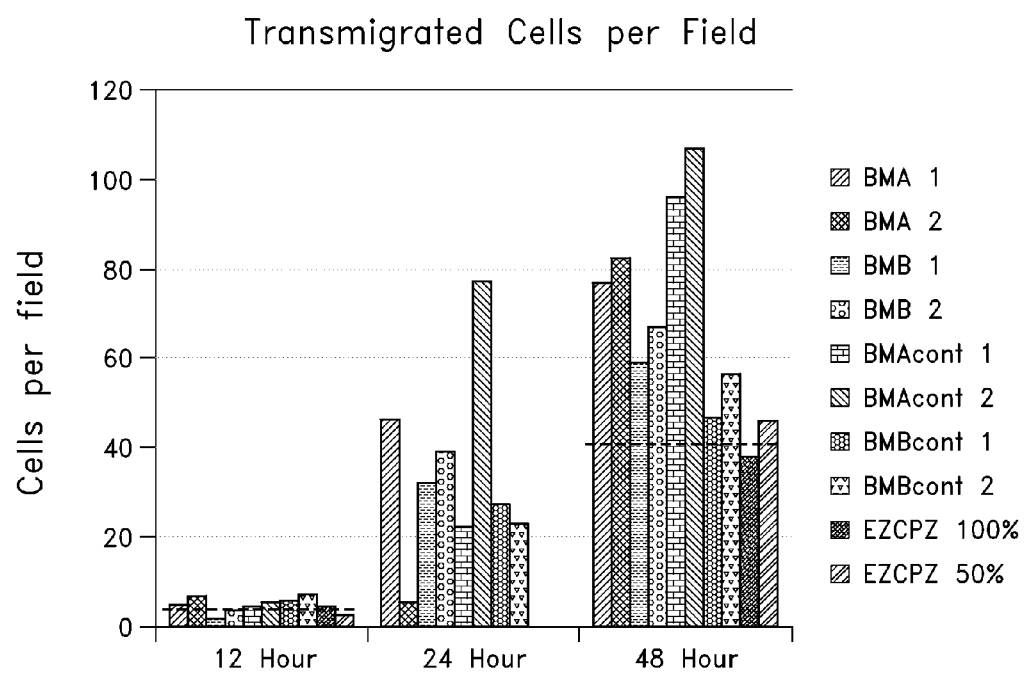
FIG. 2 is a graph showing the estimated cell counts per 100× magnification of cells in 6 fields. BMA and BMB cells in Buffers 1&2 after and before irradiation (Control) were used to attract HUVEC cells that were CM-DiI labeled. The cell count was estimated by a visual count of 6 images (fields) at 100× magnification. The counts were averaged and plotted a shown. The dotted lines represent the average for the negative media controls. Cell numbers above that line represent increased migration due to the BMA or BMB material samples. The labels shown top to bottom correspond to the bars shown left to right for each time point.
Figure 3:
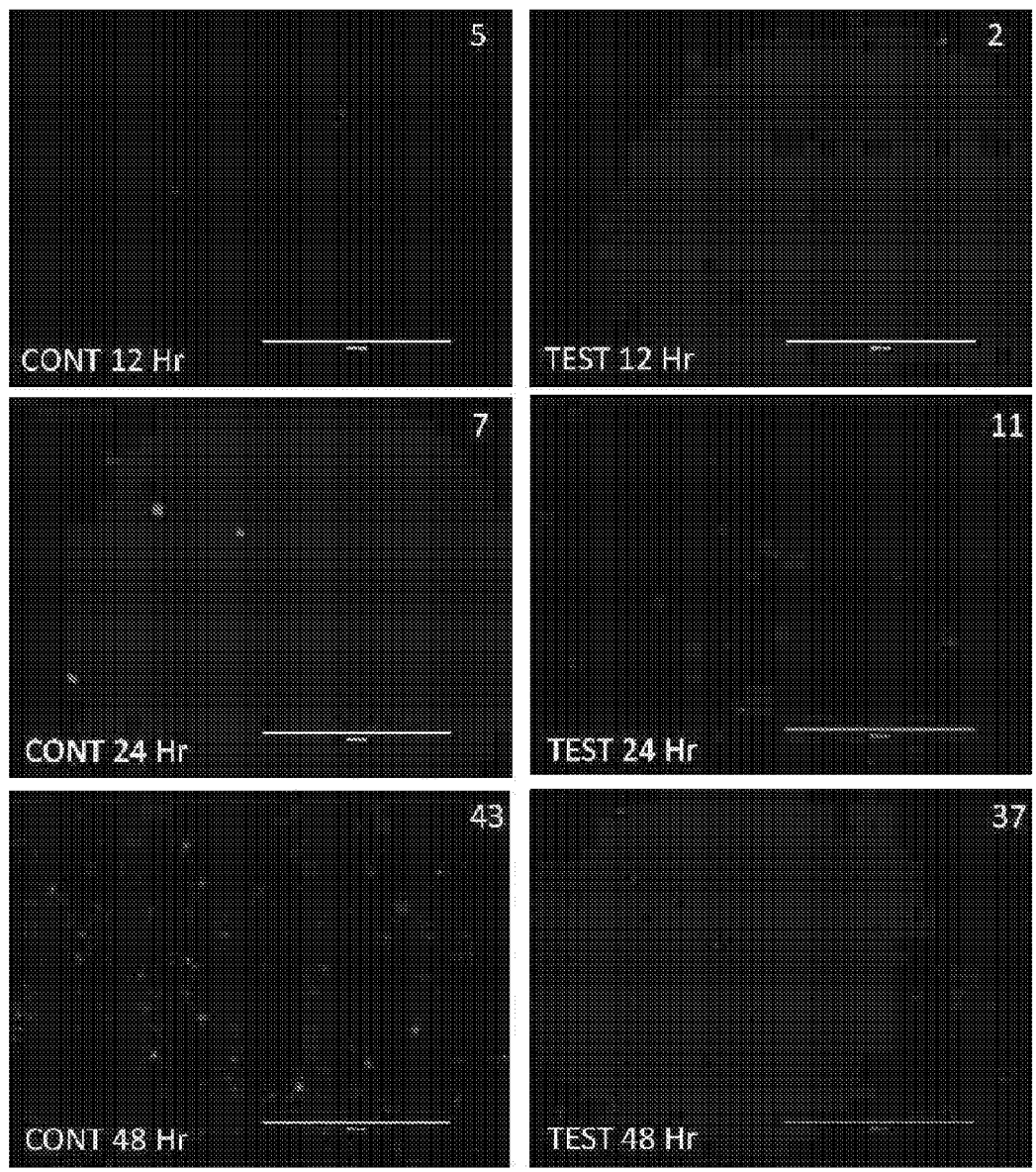
FIG. 3 shows fluorescence microscopy images of labeled human endothelial cells in the presence of BMA in Buffer 1 over a 12, 24 and 48 hour time course of transmigration.
Figure 4:
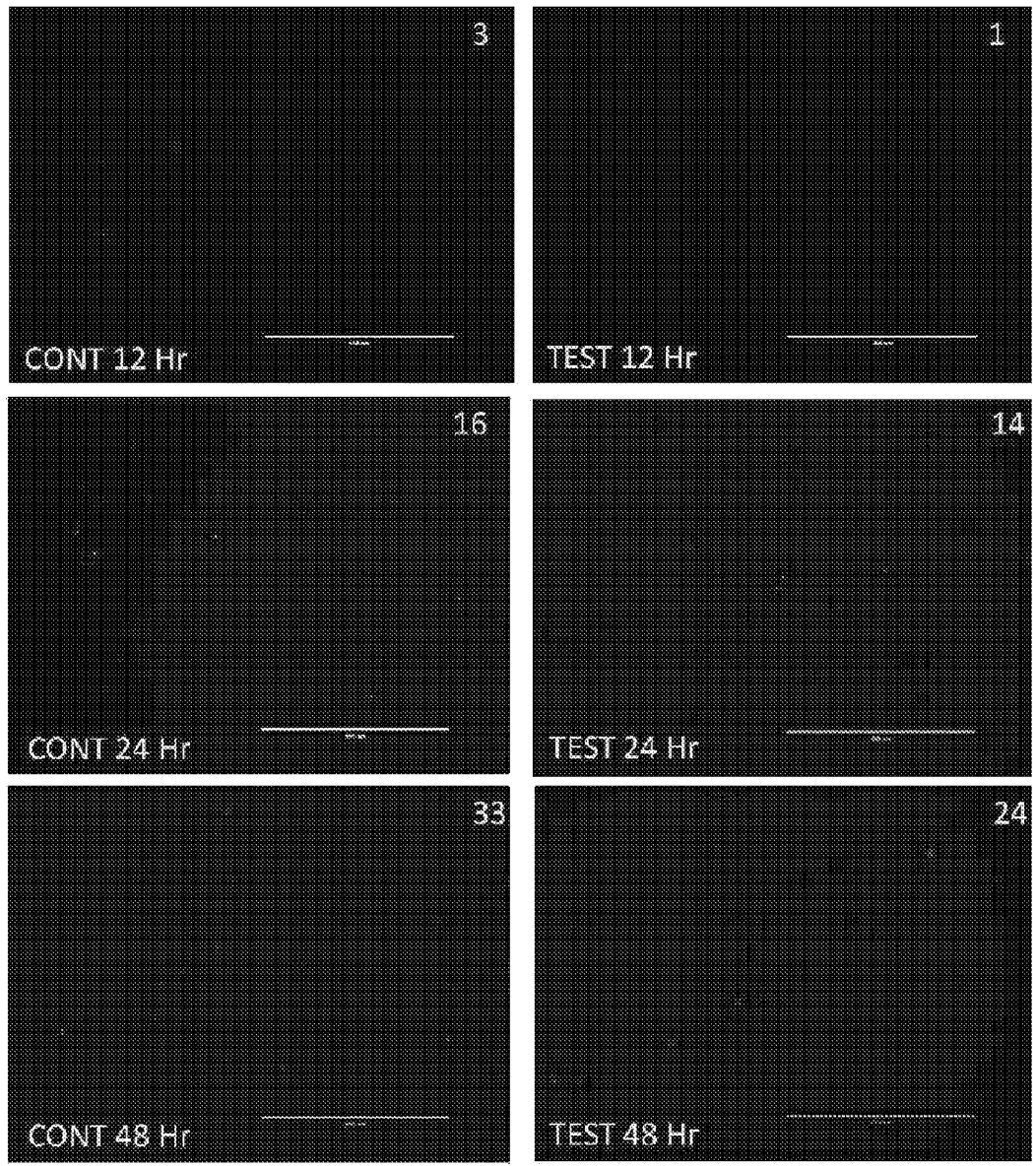
FIG. 4 shows fluorescence microscopy images of labeled human endothelial cells in the presence of BMB in Buffer 1 over a 12, 24 and 48 hour time course of transmigration.
Figure 5:
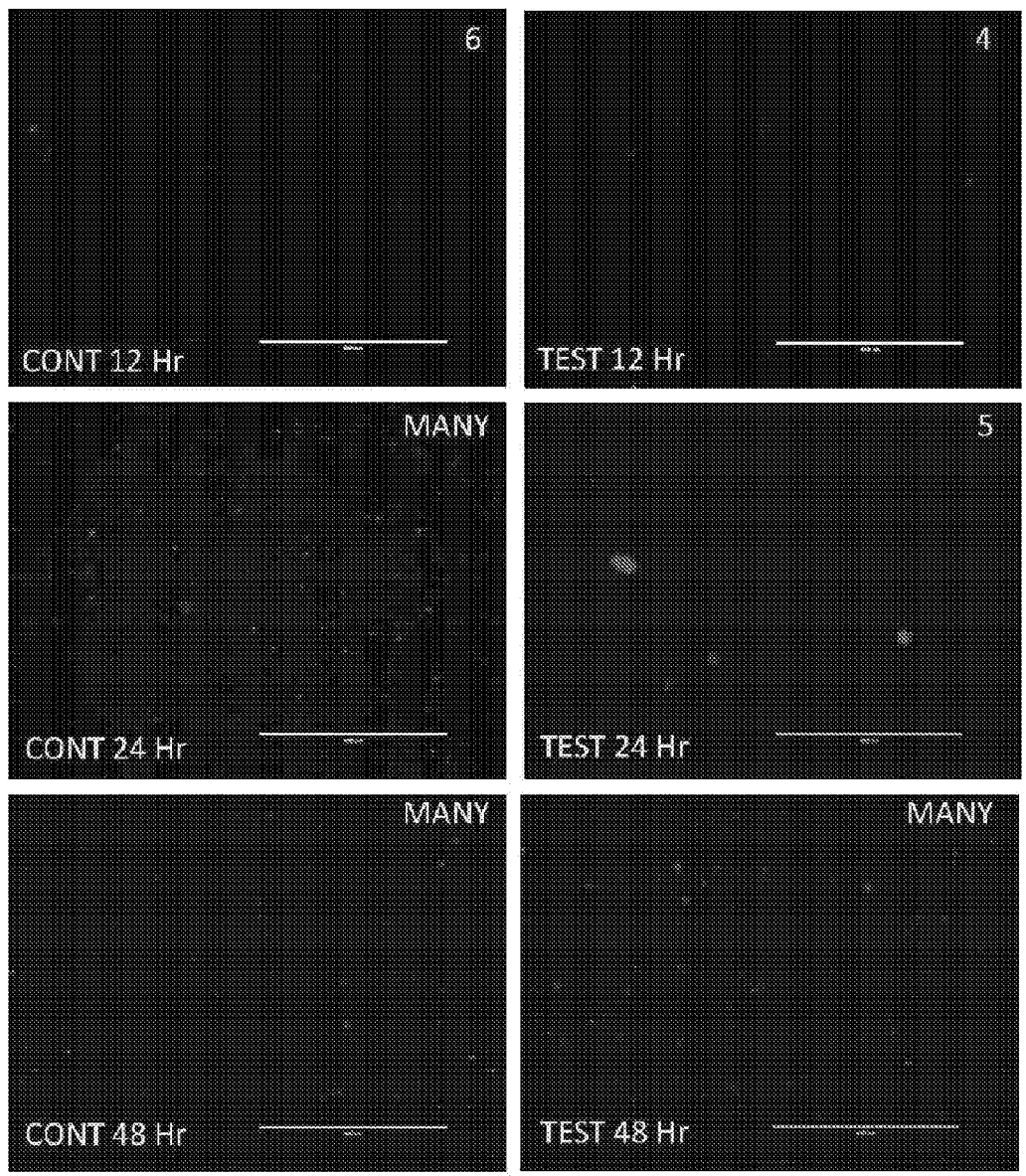
FIG. 5 shows fluorescence microscopy images of labeled human endothelial cells in the presence of BMA in Buffer 2 over a 12, 24 and 48 hour time course of transmigration.
Figure 6:
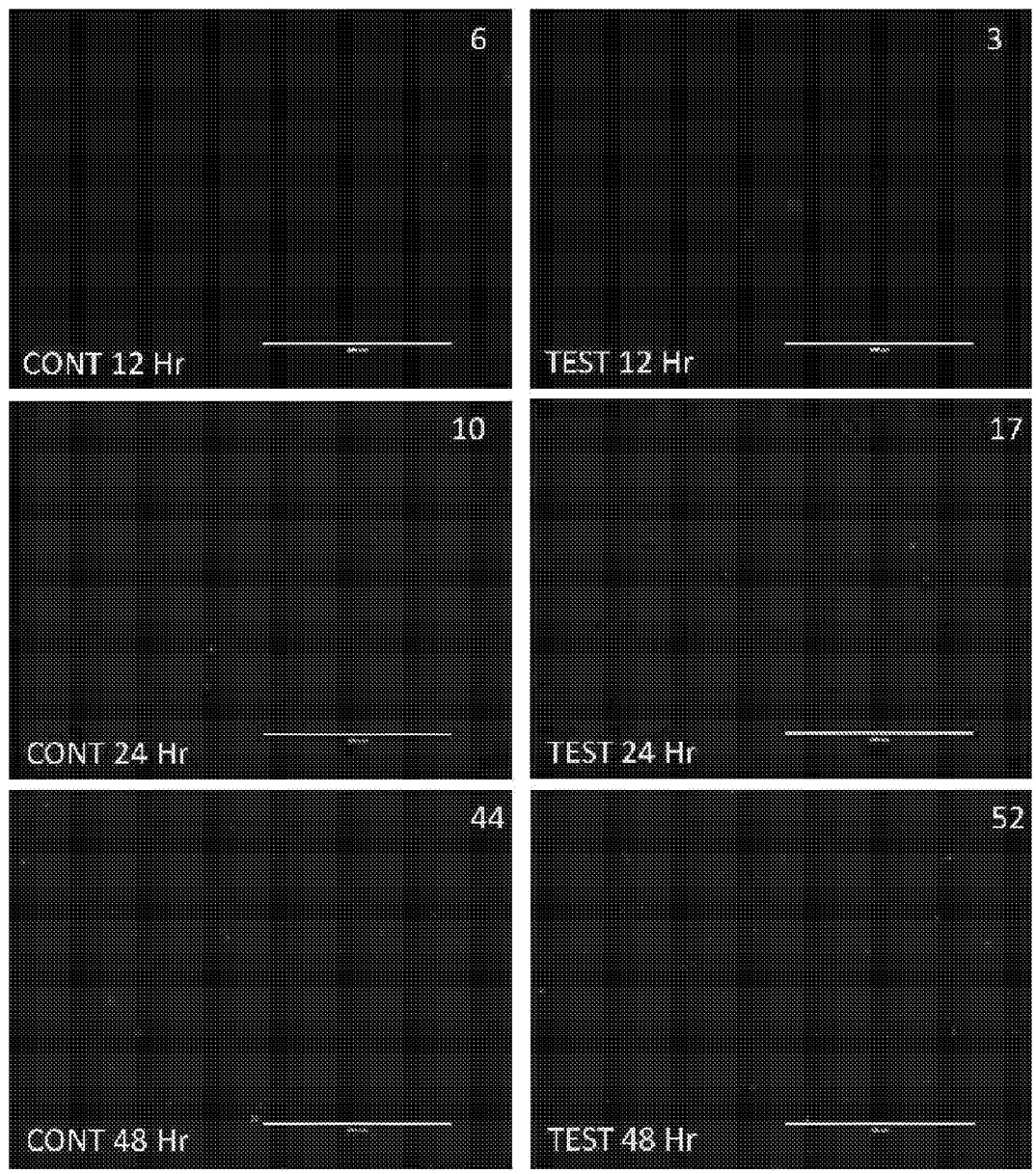
FIG. 6 shows fluorescence microscopy images of labeled human endothelial cells in the presence of BMB in Buffer 2 over a 12, 24 and 48 hour time course of transmigration.
Figure 7:
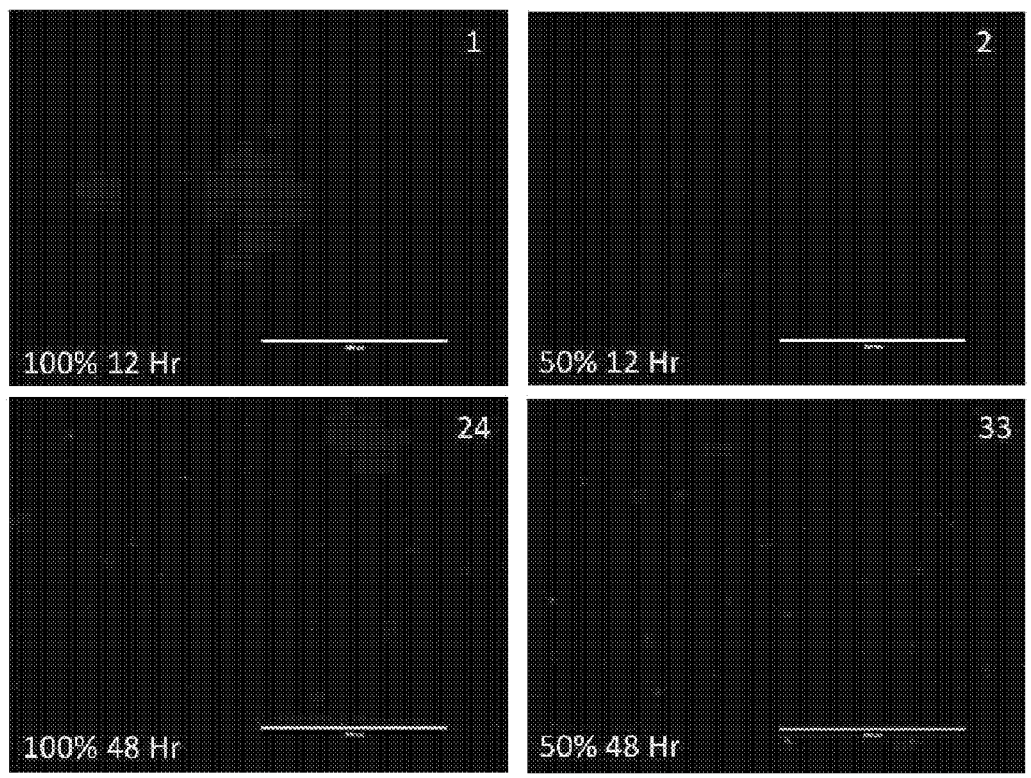
FIG. 7 shows fluorescence microscopy images of labeled human endothelial cells. The sample on the left is undiluted EZ-CPZ™, which is representative of buffers 1 & 2 in which the cells were preserved. EZ-CPZ™ is a cryopreservation media (Incell Corp., San Antonio, Tex.). EZ-CPZ™ is described by Incell Corp. as a ready-to-use, serum-free, and protein-free cryopreservation medium that is gently mixed 1:1 (v:v) with a cell suspension. EZ-CPZ™ supports high viability and re-animation of a variety of cell types including: primary cell cultures, lymphocytes, hybridoma, CHO, colon, IBHK and cancer cell lines. EZ-CPZ™ contains a proprietary formulation of clinical grade components, vitrification and cryopreservation agents, and a final concentration of 5% DMSO. EZ-CPZ™ provides cryoprotection to human and other mammalian cells. On the right is a 50:50 mixture of EZ-CPZ and M3D™ defined media (Incell Corp., San Antonio, Tex.), which is representative of the buffers in which the processed microvascular tissue composition material will be preserved in. M3D™ is described by Incell Corp. as a defined medium that contains salts, amino acids, and sugars, but no growth factors or undefined components such as serum or extracts. The time course of transmigration was imaged at the 12 and 48 hour time points.

For all of the wells, there were minimal numbers of cells in the lower chamber at the 12 hour time point. See FIG. 2 and the first row of FIGS. 3-7 as time progressed, the cells started to migrate into the lower chamber. Some of the samples were drawn to the lower chamber more quickly. The BMA samples tended to attract cells more than the BMB as seen in FIG. 2. BMA Buffer 2 test group had the lowest cell number at 24 hours but the highest cell counts at the 48 hour time point among the test samples. Overall the BMA samples worked better than the BMB samples with buffer 2 having exhibiting a trend (but not statistically significant) of induction of higher migration rate than buffer 1.

The other noticeable effect of the assay was the trend for a decrease in the migration irradiation caused in BMA of about 20%, whereas BMB had little effect and was essentially the same level (the difference was not statistically significant) at 24 and 48 hours.

The EZ-CPZ™ media control did have some transmigration but only later in the time course and to a lesser degree than the BMA and BMB samples. These results demonstrate dramatically that the cells do not have to be viable or autologous for the composition to induce an angiogenic activity.

Figure 8:
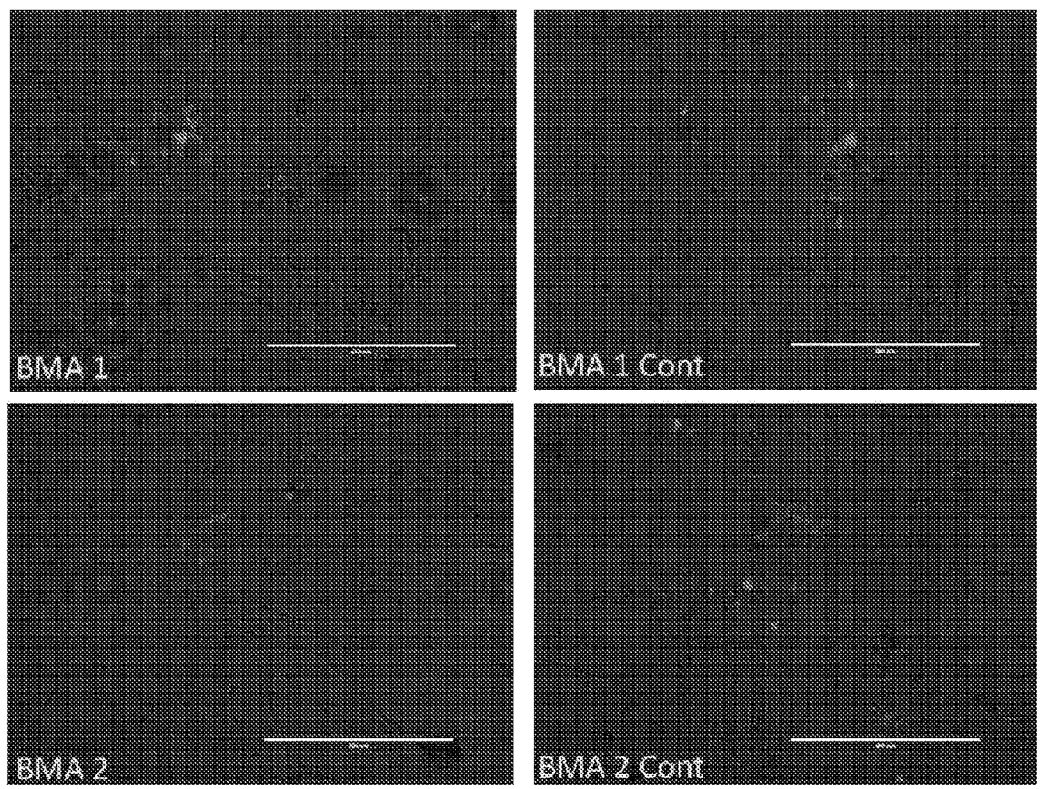
FIG. 8 shows fluorescence microscopy images. SVF cells were plated in a 48 well plate and grown to approximately 50% confluence. BMA material was stained with CMDiI and rinsed. 50 µl of the BMA material was put onto a single well of growing SVF cells. Fluorescence is observed where the SVF cells have taken up the CMDiI stained material and incorporated it into their own membranes. BMA material in Buffer 1 is depicted in the top row, and BMA material in Buffer 2 is depicted in the bottom row. The material on the left side was irradiated and the material on the right side (Cont) was not irradiated.
Figure 9:
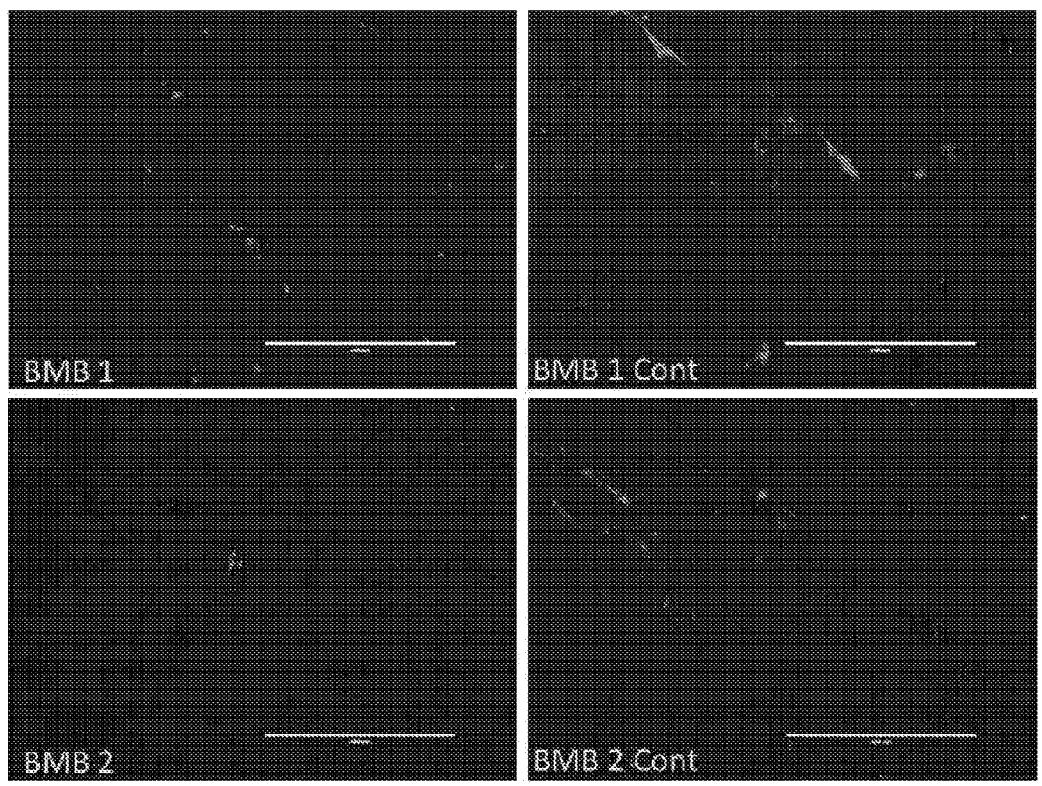
FIG. 9 shows fluorescence microscopy images. SVF cells were plated in a 48 well plate and grown to approximately 50% confluence. BMB material was stained with CMDiI and rinsed. 50 µl of the BMA material was put onto a single well of growing SVF cells. Fluorescence is observed where the SVF cells have taken up the CMDiI stained material and incorporated it into their own membranes. BMB material in Buffer 1 is depicted in the top row, and BMB material in Buffer 2 is depicted in the bottom row. The material on the left side was irradiated and the material on the right side (Cont) was not irradiated.

Uptake of Labeled Processed Microvascular Tissue Composition Microvesicles by SVF Cells This assay was performed to determine if processed microvascular tissue composition MVs were transported into SVF (stromal vascular fraction) cells. The assay was performed by labeling the remaining 100 µl of processed microvascular tissue composition material in each vial with CM-DiI, which incorporates into cell membranes even if the cells themselves are dead. The SVF cells were plated in a 48 well plate with M3D:10 media and allowed to adhere and grow until they were approximately 50% confluent. The 50 µl of the labeled material was added to the wells and incubated for 6 hours. The wells were rinsed 3 times with M3D™ and fixed with wet-mount. Images showed that several of the cells did indeed take up the material as the dye was transferred to the SVF cells as seen in FIGS. 8 and 9.

DISCUSSION

The BMA and BMB lyophilized material with or without irradiation acted as chemo-attractants to endothelial cells in this assay. A mild decrease in cell transmigration when the material was irradiated was noticed. The difference between buffers 1 or 2 was negligible.

The BMA and BMB material was taken up by living SVF cells when the material was placed on top of an already growing culture and incubated for 24 hours.

There are several important concepts illustrated with these experiments. Although the SVF samples showed huge cell losses and no viability following lyophilization, they retained more biological activity than the bone marrow samples, which showed no cell losses and viability of 10 to 50%. (The SVF cell loss may have been caused by excessive enzyme activity during the digestion step.) Both cell preparations were stable for over a year. Sterilization did not materially affect their ability to attract endothelial cells.

TABLE 15

Growth Factors, Receptors, Hormones, Genes, Transcription Factors Associated with Bone
GROWTH FACTORS AND RECEPTORS

| Identity | Example Source | General Description |
|---|---|---|
| TGF-β SUPERFAMILY | | |
| TGF-β 1 | Genentech, Chiron, Collagen/Celltrix, | soft and hard tissue wound healing, oncology, hematopoiesis, latent form of TGF-beta binds mannose-6-P receptor, colon and pancreatic cancers |
| TGF-β 2 | Genzyme T.R., Celltrix | macular holes, ulcers, oncology), betaglycan |

TABLE 15-continued

Growth Factors, Receptors, Hormones, Genes, Transcription Factors Associated with Bone
GROWTH FACTORS AND RECEPTORS

| Identity | Example Source | General Description |
| --- | --- | --- |
| TGF-β 3 | Oncogene (B-M-Squibb) | Oncology, skeletal |
| TGF-β 4 | (chicken) | |
| TGF-β 5 | | |
| TGF-βR 1-3 | | Type III receptor aids binding to Type II receptor |
| BMP 2 | Genetics Institute | KO lethal, expressed in tooth pulp |
| BMP 3 (osteogenin) | Urist, Reddi | Aka osteogenin, G.I., expressed in lung |
| BMP 4 (2a) | | KO lethal, expressed in lung, tooth: overexpr. = bone thickening (neonates) |
| BMP 5 | | expressed in lung, short ear mutant mouse has bone deformities |
| BMP 6 (vgr-1) | | expressed in lung, KO delayed ossification of sternum (mild phenotype) |
| BMP 7 (OP-1) | Creative Biomolecules | KO kidney, eye; expressed in tooth pulp |
| BMP 8 (OP-2) | Creative Biomolecules | tooth pulp |
| BMP 9 (OP-3) | Creative Biomolecules | |
| BMP 10 | | |
| BMP 11 | | |
| BMP 12 (GDF-7) | | G.I. Promoted cartilage and tendon growth, P-T repair |
| BMP 13 (GDF-6, CDMP-2) | | G.I. Promoted cartilage and tendon growth |
| BMP 14 | | |
| BMP 15 | | G.I. |
| BMPR IA | | Type IA upregulates Type IB, KO ectopic bone and cartilage (no pheno in another lab) |
| BMPR IB | | Activating IB gives cartilage (even ectopic); KO no cartilage. |
| BMP2R | | Type II receptor binds to type IA (increase nodules) or IB (less nodules) |
| GDF 1 | | expressed in brain, tooth pulp |
| GDF 2 | | |
| GDF 3 (Vgr-2) | | |
| GDF 4 | | |
| GDF 5 (MP52, CDMP-1) | | soft tissue, tooth pulp, bone and cartilage |
| GDF 6 (BMP-13, CDMP-2) | | tendon, ligament, cartilage, thicker and longer bones (Gene TX to increase production in neonates), tooth pulp |
| GDF 7 (BMP-12) | | cartilage and tendon, tooth pulp |
| GDF 8 (myostatin) | MetaMorphix | KO allows 2-3X muscle mass increase |
| GDF 9 | | |
| GDF 10 | | Membranous bone, adipose tissue |
| Dpp | | Fruit fly protein analagous to BMP 2 and OP-1, Induces bone, cartilage, and bone marrow in mammals |
| 60A | | Fruit fly protein analagous to BMP 2 and OP-1, Induces bone, cartilage, and bone marrow in mammals |
| MP52 | | Differentiation of mesenchymal progenitors, soft tissues, tooth pulp |
| univin | | |
| Vg1 | | |
| Vgr-1 (BMP-6) | | Expressed in lung |
| Vgr-2 (GDF3 | | |
| nodal | | |
| fugacin | | |
| ADMP | | |
| dorsalin-1 | | |
| PC-3 | | |
| radar | | |
| screw | | |
| lefty | | |
| GDNF | | Expressed in tooth pulp |
| α-inhibin | | KO's develop gonadal then adrenal tumors |
| inhibin β$_A$ | | |
| Inhibits βB | | |
| Inhibin βC | | |
| Inhibin βD | | |

TABLE 15-continued

Growth Factors, Receptors, Hormones, Genes, Transcription Factors Associated with Bone
GROWTH FACTORS AND RECEPTORS

| Identity | Example Source | General Description |
|---|---|---|
| MIS | | Mullerian Inhibiting Substance |
| CDMP 1 | | Increases chondrogenesis and osteogenesis in vitiro, subQ cartil. and bone |
| CDMP 2 | | Increases chondrogenesis in vitro, subQ cartil. and bone in vivo. |
| OGP Osteogenic peptide (I. Bab). | | Trauma factor which induces bone. 14-mer, last 5 AA's are essential. |
| TGF-α | | Soft tissue wound healing, similar to EGF |
| PDGF AA | Chiron, Creative Biomolecules | Chiron Phase III clinical showed 50% reduction in wound size at 28 days, in clinicals for periodontal disease |
| PDGF BB | Zymogenetics | cartilage repair |
| PDGF AB | | |
| CTGF (connective tissue growth factor) | | Binds to PDGF-BB receptor on 3T3 cells |
| CEF 10 | | 45% homology to CTGF |
| EGF | | Closely related actions to TGF-α |
| HB-EGF | | Related to TGF-α, potent in wound healing |
| Pleiotrophin (HB-GAM) | | Induced bone and cartilage in rat calv defect |
| VEGF | | Vascular Endothelial Growth Factor -- secreted by osteoblasts |
| FGF-1 (aFGF) | | Receptor interactions with heparin, polyanions, matrix molecules (heparan sulphate) are important in action and regulation of the FGFs |
| FGF-2 (bFGF) | | Synergen clinical study on soft tissue healing (poor results) Mundy showed bone formation following systemic injection. Orquest licensed from SCIOS, hyal acid carrier Ossigel inject for fracture repair |
| FGF 3-6 | | Oncogene products |
| FGF-7 (KGF) | | Mesenchymal stimulation of skin growth and healing (keratinocytes) |
| FGF-8 | | |
| FGF-9 | | |
| FGF-18 (Zfgf5) | Zymogenetics | Shown to have chondrogenic effect in vivo |
| FGFR 1-4 | | |
| NGF | | |
| Osteopontin | Metra (Orquest) | possible induction of osteoprogenitors |
| Osteopoietin | | Growth Hormone, acts via IGF-I |
| IGF I (somatomedin C) | Genentech, Cephalon | skeletal growth and protein metabolism, bone formation when infused in rats |
| IGF II | MSA | Embryogenesis, Form most common in mammals > rats |
| IGFBP 1 | | |
| IGFBP 2 | | |
| IGFBP 3 | Celltrix | Increased bone mass local and systemic |
| IGFBP 4 | | |
| IGFBP 5 | Chiron, Baylink, BMGmbh | |
| IGFBP 6 | | |
| LDGF | | |
| TNF-α | | |
| INFα | | |
| INFβ | Chiron, Betaseron | marketed for MS |
| INFγ | | consensus Genentech in clinical trials |
| CSF-1 | | Required for osteoclast formation |
| IL-4 | | Inhibits OB function |
| IL-6 | Imclone, Sandoz, Serono | Made by and activates OB and O'clst, (2Xgp130) receptor |
| IL-8 | | |
| IL-11 | | [2Xgp130] receptor |
| LIF (Leukemia Inhibitory Factor) | | made by and activates OB, [LIFR + gp130] |
| Oncostatin-M [OSMR + gp130 or LIFR + gp130] | | activate OB, increase differentiation |
| Cardiotrophin-1 [LIFR + gp130] | | increase nodule formation |
| CNTF [LIFR + gp130] | | |

TABLE 15-continued

Growth Factors, Receptors, Hormones, Genes, Transcription Factors Associated with Bone

GROWTH FACTORS AND RECEPTORS

| Identity | Example Source | General Description |
| --- | --- | --- |
| ACTIVIN βA | | Tooth pulp |
| ACTIVIN βB | | Tooth pulp |
| Noggin | Regeneron, P&G | Binds to BMP's and antagonizes actions |
| BNP (brain natriuretic peptide) | Scios | Increased chondroprogenitors in vivo, |
| ROBO-1 | Glaxo | Upregulated when vertebrae stretched, 37 kd, estrogen raises, PTH lowers |
| VEGF-1 | | Einhorn found expression during Ilzarov technique |
| BSP (bone sialoprotein) | | Healed calvaria defect when immobilized to gelatin |
| Osteopontin | | Induced bone formation in rat calv defect |
| Endothelin 1 | | Expressed by OB and chondro (and endothelial), both have receptors. |
| Endothelin 3 | | induced bone and cartilage formation in rat calv |

HORMONES

| | | |
| --- | --- | --- |
| PTH | | |
| PTHR | | |
| PTHrP | | Signals from the perichondrium to receptors in the growth plate chondrocytes to prevent hypertrophic differentiation = negative feedback for Ihh, Bcl-2. |
| PTHrP(107-111) | | bone induction region. KO lethal all cartilage ossified and fused, Overexpress causes massive cartilage onlages |
| Vitamin D metabolites | | |
| Vitamin DRs | | |
| Calcitonin | | |
| Estrogen | | Raises prolif. and differn. of marrow cells, less adipogenesis |
| RA (retinoic acid) | | Differentiation |
| RAR | | α, β, γ receptors in nucleus. α and γ involved in cartilage formation |
| T4 (thyroid) | | Speeds differentiation of growth plate |
| GH (growth hormone) | | Delays differentiation of growth plate |
| PGE 1 | | Local infusion caused bone formation |
| PGE 2 | | |
| EB 2 | | PG receptor on marrow cells |
| EB 4 | | PG receptor on bone progenitors |

MISCELLANEOUS

PGP
CTAP-III
b-TG
NAP (1-3)
PF-4
MGSA
GRO
IP10
C9E3
CEF-4
MMP-2

GENES

| | | |
| --- | --- | --- |
| HoxA-1 | | |
| HoxA-2 | | Second branchial arch, craniofacial elements |
| HoxA-3 | | |
| HoxA-4 | | |
| HoxA-4 | | |
| HoxA-6 | | |
| HoxA-7 | | |
| HoxA-9 | | Shoulder |
| HoxA-10 | | Humerus |
| HoxA-11 | | Radius-ulna |
| HoxA-13 | | phalanges |
| HoxB 1 | | |
| HoxB 2 | | |
| HoxB 3 | | |
| HoxB 4 | | |
| HoxB 5 | | |

TABLE 15-continued

Growth Factors, Receptors, Hormones, Genes, Transcription Factors Associated with Bone

GROWTH FACTORS AND RECEPTORS

| Identity | Example Source | General Description |
|---|---|---|
| HoxB 6 | | |
| HoxB 7 | | |
| HoxB 8 | | |
| HoxB 9 | | Shoulder |
| HoxB 13 | | Phalanges |
| HoxC 4 | | |
| HoxC 5 | | |
| HoxC 6 | | |
| HoxC 8 | | |
| HoxC 9 | | shoulder |
| HoxC 10 | | Humerus |
| HoxC 11 | | Raidus-ulna |
| HoxC 12 | | Metacarpals |
| HoxC 13 | | Phalanges |
| HoxD 1 | | |
| HoxD 3 | | |
| HoxD 4 | | |
| HoxD 8 | | |
| HoxD 9 | | Shoulder |
| HoxD 10 | | Humerus |
| HoxD 11 | | Radius-ulna |
| HoxD 12 | | Metacarpals |
| HoxD 13 | | phalanges, Homeobox gene, 4th sacral vertebra |
| Shh (Sonic hedgehog) | | skeletal patterning, induces FGF-4, BMP-2&4, HoxD-13 |
| Ihh (Indian hedgehod) | | similar activity and signaling to Shh, regulates (prevents) hypertrophic differentiation, (−) feedback via PTHrP, induces BMP2, PTC, GLI, HOXD-11, HOXD-13, represses collagen type X and BMP-6. |
| Dhh (Desert hedgehog) | | spermatocyte survival |
| Pax 1 | | KO slight phenotype |
| Pax 2 | | |
| Pax 3 | | |
| Pax 4 | | |
| Pax 5 | | |
| Pax 6 | | |
| Pax 7 | | |
| Pax 8 | | |
| Pax 9 | | KO gave no teeth or thymus, cleft palate, and extra thumb |
| WNT 5A | | Proximal-distal outgrowth of limbs under control of apical ectodermal ridge and FGF |
| WNT 7A | | Dorsal-ventral patterning via LMX-1a |
| LMX 1a | | Dorsal-ventral patterning, activated by WNT-7a and repressed by En-1 |
| En 1 | | Dorsal-ventral patterning |
| MSX 1 (Hox7) | | Homoebox gene involved in growth of intramembranous bone, reg'd by BMP-4. KO mild pheno unless MSX-2 also KO'd |
| (Hox8, 1) | | Transcription factor, homeobox gene, involved in suture closure, reg'd by BMP-4. Bone site specific even in adults. Inhibits chick OB differn. EtOH blocks msx-2 expression in development. KO mild pheno unless MSX-1 also KO'd |
| MSX 3 | | |
| c-jun | | |
| c-ras | | |
| junb | | |
| egr-1 | | |
| c-src | | Gene required for OC's to resorb bone |
| c-fos | | Gene required for OC's to form |
| dHand | | |
| eHand | | |
| twist | | |
| ID | | |
| Permo-1 | | |

TRANSCRIPTION FACTORS

| Identity | Example Source | General Description |
|---|---|---|
| *bHLH | | Family of transcription factors triggering lineage commitment (eg MyoD) |
| paraxis | | earliest marker of cells which will become somites, epithelial marker? |

TABLE 15-continued

Growth Factors, Receptors, Hormones, Genes, Transcription Factors Associated with Bone
GROWTH FACTORS AND RECEPTORS

| Identity | Example Source | General Description |
|---|---|---|
| scleraxis | | prefigures the skeleton after paraxis, but KO doesn't form somites. Overexpression favors chondrocyte pheno |
| CK-ERG | | Precedes formation of cartilage |
| SOX9 | | Transcription factor, bowed long bones, related to SRY |
| MAD-1 | | BMP-2 signal in C2C12 |
| AP-1 | | TGF |
| NF-1 | | TGF |
| SP-1 | | TGF |
| SP-2 | | |
| SP-3 | | TGF |
| TIEG | | TGF, estrogen |

Example 8—In Vitro and In Vivo Effects of Microvascular Tissue

As discussed above, various stem cell preparations have shown beneficial effects in animal and clinical studies for a variety of indications. In many instances, the survival of the administered stem cells is relatively poor. The present studies were therefore designed to address whether, as discussed in relation to several embodiments above, viable stem cells are needed in order to achieve some (or all) of the therapeutic benefits associated with stem cells. The present study employed, microvascular tissue, a rich source of stem and progenitor cells, that was processed according to the methods disclosed above.

In brief, microvascular tissue was isolated from human cadaveric adipose tissue by mincing the tissue and subsequently enzymatically digesting the minced tissue. The digested tissue was then centrifuged to remove fat, resulting in microvascular tissue. The microvascular tissue was resuspended in a cryopreservation buffer (1:1 mix of M3:DC and EZ-CPZ medias, INCELL Corporation, San Antonio, Tex.), dispensed into vials, and lyophilized or both lyophilized and radiation sterilized.

The resulting processed microvascular tissue was assayed for cell counts, viability, phenotype, CFU-F, and bioactivity in angiogenesis and orthopedic models.

Results

The cell counts and viability of freshly isolated, lyophilized and lyophilized/sterilized microvascular tissue is shown in Table 16. The phenotype of each preparation is shown in Table 17.

TABLE 16

| Preparation | Isolated | Lyophilized | Lyophilized + Sterilized |
|---|---|---|---|
| Cell Count (DAPI/gram of fat) | 1.2 ± 0.2 million | 0.9 ± 0.1 million | 1.0 ± 0.3 million |
| Viability (Trypan Blue) | 85 ± 5% | 15 ± 1% | 2 ± 1% |

TABLE 17

| Phenotype | Type IV Collagen | CD31+ | CD34+ | CD44+ | CD45+ |
|---|---|---|---|---|---|
| Fresh Microvascular Tissue | 65 ± 5% | 52 ± 7% | 58 ± 4% | 55 ± 10% | 5 ± 1% |
| Lyophilized + Sterilized | 85 ± 13% | 73 ± 17% | 65 ± 9% | 61 ± 13% | 11 ± 3% |

The cell count/cell viability data clearly demonstrate that there is not a significant change in cell number based on the processing of the microvascular tissue (e.g., whether fresh, dried, or dried and sterilized, the cell counts are roughly equivalent, based on nuclear uptake of DAPI DNA stain). However, lyophilization of the microvascular tissue significantly reduces the ability of the cells in the microvascular tissue to exclude trypan blue. Lyophilization induces approximately a 70% reduction in the percentage of viable cells. Exposure to radiation further reduced the viability, such that only approximately 2% of the cells in the microvascular tissue were viable. Further, when assayed for functional mesenchymal stem cells (using an established colony-forming unit-fibroblast (CFU-F) assay), no functional mesenchymal stem cells were detected in the lyophilized or the lyophilized/sterilized preparations.

Interestingly, despite the unchanged cell number and the reduction in viability, the various processing methods altered the phenotype of the cells. As shown in Table 17, Type IV collagen increased modestly (versus a fresh preparation) in lyophilized/sterilized microvascular tissue. This data suggests that the lyophilized/sterilized microvascular tissue may be well-suited for repair of soft tissues, due at least in part to its increased collagen density. Collagen-based materials have been tested for their use in tissue-engineering, however the microvascular tissue disclosed herein is particularly advantageous because of the ready availability of the material, and its enhanced "stemness" (discussed below). Each of the established hematopoietic stem cell markers CD31 (hematopoietic stem cells), CD34 (bone marrow/hematopoietic stem cells), CD44 (cancer stem-like cells) and CD45 (hematopoietic stem cells) were essentially were upregulated in response to lyophilization and sterilization. Thus, despite a nearly complete reduction in the viability of the cells in lyophilized/sterilized microvascular tissue, any cells remaining have enhanced expression of markers known to be expressed by stem cells. As such, the lyophilized/sterilized microvascular tissue may be more suited to tissue regeneration because of this enhanced stemness (and the indirect effects that the increased stemness induces, e.g., paracrine recruitment of other endogenous cells that enhance repair, release of growth factors from the microvascular tissue, etc.).

Figure 10:
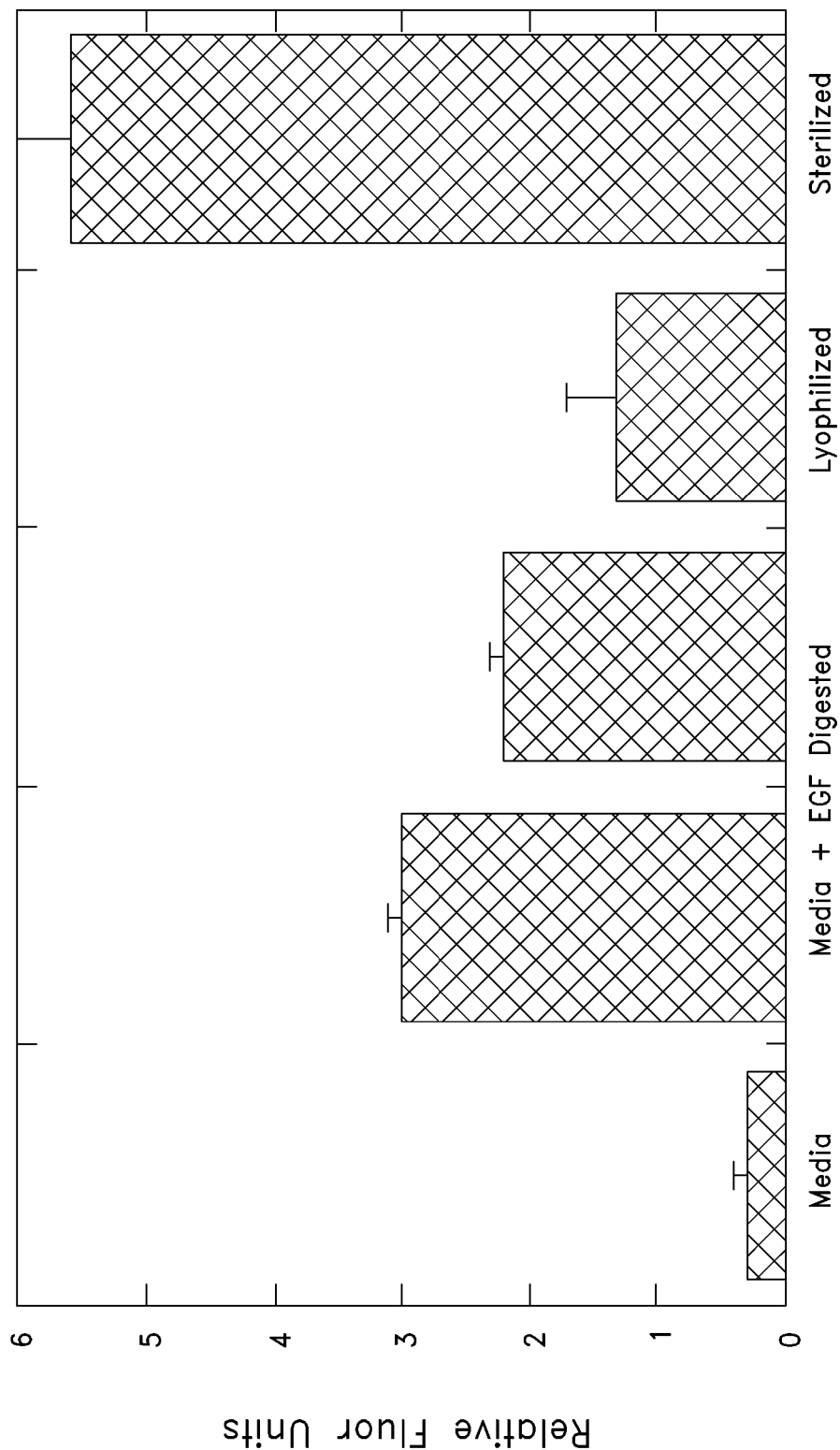
FIG. 10 depicts data related to the migration of human umbilical vein endothelial cells (HUVEC) cells in response to exposure to microvascular tissue. The number of HUVEC's crossing the membrane of a Transwell plate was counted at 48 hrs and compared to culture media+EGF controls.

The various microvascular tissues were evaluated for their ability to recruit other types of cells. Recruitment of cells can enhance the repair or regeneration of damaged or diseased tissue by a variety of mechanisms. For example, recruitment of endothelial cells can enhance blood vessel formation, thereby improving blood supply that facilitates new tissue formation. Recruitment of endogenous stem cells can initiate a cascade of events that foster new tissue growth and/or repair of existing damaged tissue. Human umbilical vein endothelial cells (HUVEC) labeled with DiI and were placed in the top of Transwell plates with various types of microvascular tissue in the bottom wells. The number of HUVEC's crossing the intra-well membrane was counted for each type of microvascular tissue after 48 hours and compared to culture media alone or media supplemented with epidermal growth factor (EGF) as controls. FIG. 10 depicts the results. Little migration of HUVEC cells was detected in response to media alone. EGF, which is established as an inducer of HUVEC migration result in about 10 times more migration that media alone. Freshly isolated microvascular tissue ("digested" in FIG. 10) induced slightly less migration than EGF, and lyophilized induced even less migration (though it was still greater than media alone). Unexpectedly, lyophilized/sterilized microvascular tissue induced nearly 2 times more migration as compared to EGF, and nearly 20 times more than media alone. Thus, the drying and sterilization of microvascular tissue significantly enhances its ability to recruit cells in vitro. That enhanced ability, in several embodiments, provides, at least in part, enhanced tissue repair and/or regeneration in vivo.

Figure 11:
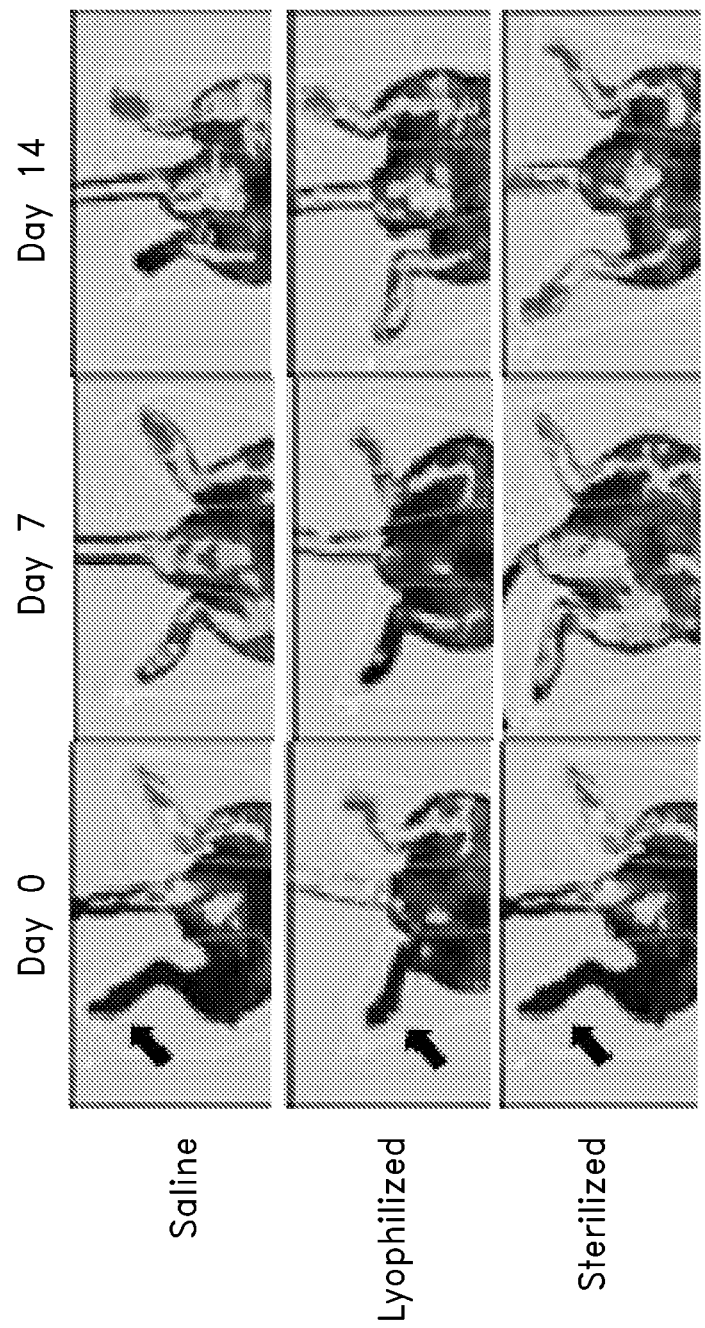
FIG. 11 depicts data related to the restoration of blood flow to the hindlimbs of mice after femoral artery transection at day 0, and days 7 and 14 after administration of either lyophilized or sterilized microvascular tissue.

That enhanced repair in vivo was corroborated by demonstrating that lyophilized/sterilized microvascular tissue induces a more robust and rapid restoration of blood flow to tissue that was rendered ischemic. SCID mice were subjected to unilateral ligation and transection of the femoral artery according to established methods in order to replicate ischemia (a condition that leads to severe tissue damage). Microvascular tissue processed in various ways was introduced into the ischemic limb on day 0, 3, and 7, and the mice were imaged by laser doppler on days 0, 7, and 14. As shown in FIG. 11, control animals injected with saline show little restoration of blood flow (the ischemic limb is designated with an arrow) after 7 or 14 days. In contrast, lyophilized microvascular tissue resulted in at least partial restoration of blood flow by 14 days. However, lyophilized/sterilized microvascular tissue resulted in significant increases in blood flow by 7 days, with blood flow at 14 days largely indistinguishable from the contralateral control limb. These data corroborate the in vitro migration data and indicate that, in several embodiments, the lyophilized/sterilized microvascular tissue can enhance restoration of blood flow.

In several embodiments, the restoration of blood flow is due, at least in part, to formation of new blood vessels, including small vessels (e.g., microvasculature), medium vessels, and large diameter vessels (e.g., those that are major suppliers of blood to a tissue). Matrigel (0.5 mL) was mixed with saline or microvascular tissue (human) to generate a microvascular tissue implant, which was injected subcutaneously into SCID mice. After 14 days the implants were removed, fixed, and stained with α-CD31 fluorescent antibody. Blood vessels that had infiltrated the implants were sized and counted with a microscope. Standard deviations were 12-30% of average counts/field. 2 doses of tissue were tested after each processing step. There were no human $CD31^+$ cells found.

Figure 12:
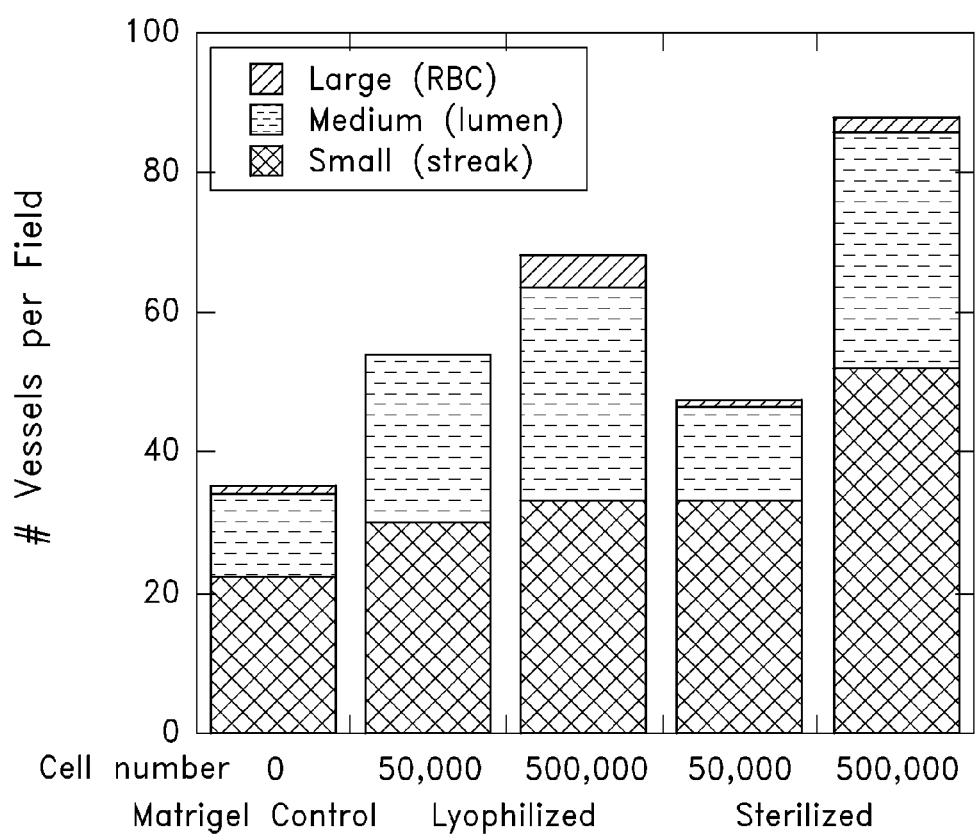
FIG. 12 depicts data related to the generation of new blood vessels in SCID mice after injections with matrigel alone, or in combination with either lyophilized or sterilized microvascular tissue.

FIG. 12 summarizes the data related to infiltration of various vessel sizes after implantation of microvascular tissue implants having various cell numbers and being processed in different manners. Matrigel resulted in about 35 vessels per field, the majority being small vessels. Implantation of lyophilized microvascular tissue with about 50,000 cells yielded increased infiltration, with a more robust generation of medium sized vessels. Implantation of lyophilized microvascular tissue with about 500,000 cells led to still further vessel generation, with a substantial increase in the number of large diameter vessels. Implantation of lyophilized/sterilized microvascular tissue with about 50,000 cells resulted in increased vessel numbers as compared to control, with some generation of large vessels. Implantation of lyophilized/sterilized microvascular tissue with about 500,000 cells resulted in significant vessel generation, over two times greater than control. Interestingly, as compared to the 50,000 cell dose, the larger cell number, despite the near-zero viability, yielded a number of large diameter vessels. Thus, administration of processed microvascular tissue, whether lyophilized or lyophilized/sterilized, appears to boost the formation of larger diameter vessels. These data are further supportive of the ability of microvascular tissue to enhance the migration and/or formation of blood vessels, which is an important aspect of repairing tissue. Moreover, in several embodiments, the generation of blood vessels of various sizes ensures that not only is there adequate capacity of carry blood from the main branches of the circulatory system to the target tissue (large diameter), but that blood can be effectively distributed throughout the target tissue, even to interior portions (medium and small vessels).

Taken together, these data indicate that microvascular tissue has the capacity to induce angiogenesis both in vitro and in vivo. As such, microvascular tissue is a highly attractive mechanism by which to institute tissue repair and/or regeneration, based on its ability to enhance angiogenesis, which will facilitate and/or maintain the repair and/or regeneration of tissue by ensuring adequate blood supply and nutrient/oxygen flow.

Additionally, microvascular tissue was assessed for its ability to enhance repair of bone and cartilage. With respect to bone, 8 mm×2 cm critical-sized defects were drilled into the distal metaphysis of mature goats. Tissue scaffolds (BIOFIBER, Tornier) were rolled tightly and inserted into the defects alone, or including microvascular tissue (volume of 1 ml, ~$10^6$ cells). Cells were loaded simply by adding 1 ml water to vial, swirling briefly, then dripping the contents onto a scaffold and waiting 5 min for binding. At 12 weeks the defects were compression tested and decalcified for histology.

Figure 13A:
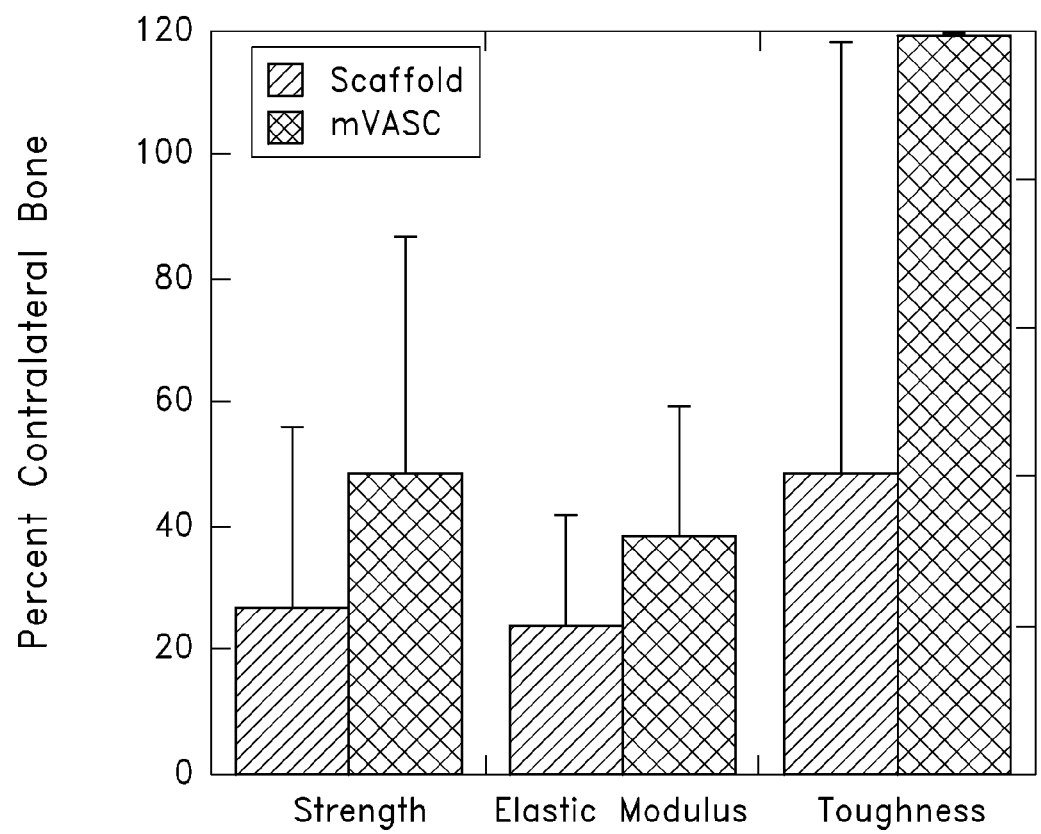
FIGS. 13A-13C relate to the regeneration of bone after implantation of microvascular tissue.
Figures 13B, 13C:
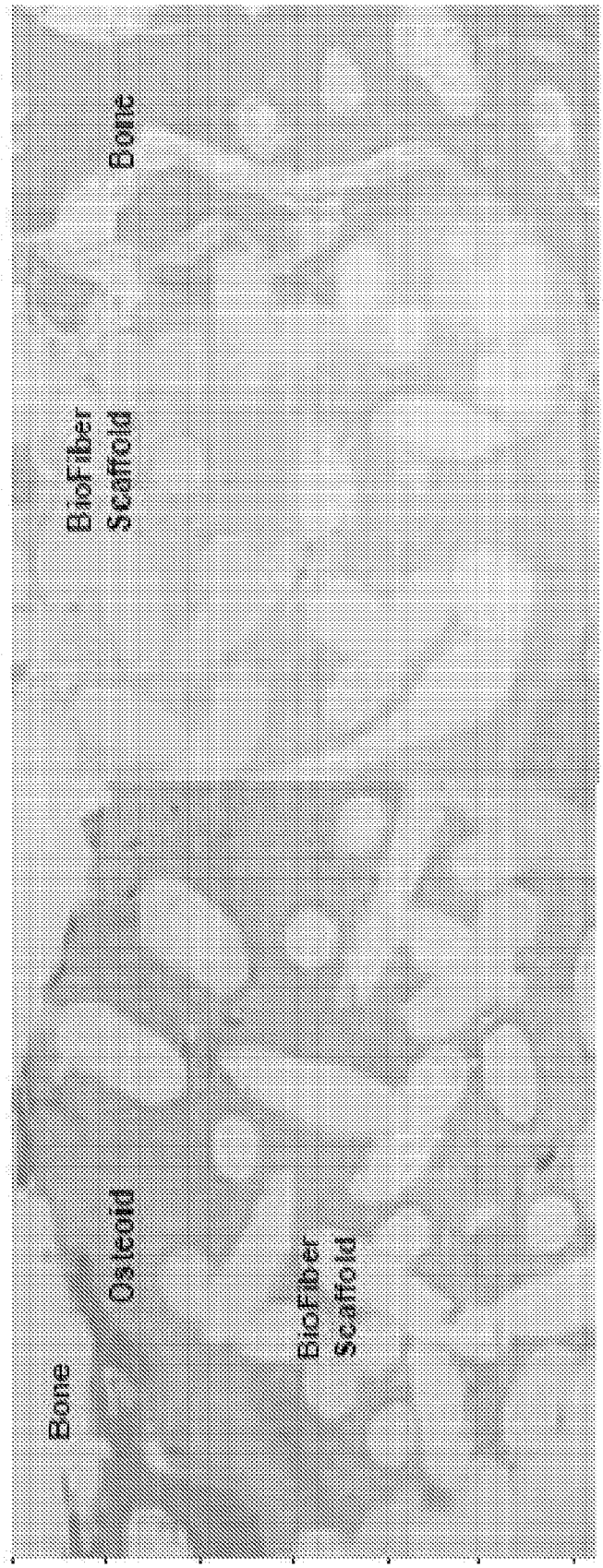

FIGS. 13A-13C show data related to the repair of bone defects. FIG. 13A shows the strength, elastic modulus, and toughness of the repaired bone as compared to the contralateral control. Use of the scaffold alone resulted in the damaged bone having approximately 20% of the strength and elastic modulus of the control bone, and roughly 50% of the toughness of the control bone. When the scaffold was supplemented with a lyophilized/sterilized microvascular tissue, each of strength, elastic modulus, and toughness was increased relative to scaffold alone. These data thus indicate, the use of microvascular tissue facilitates the repair of damage to bone. FIGS. 13B and 13C, show representative histology from bones treated with the scaffold alone and bones treated with the scaffold supplemented with microvascular tissue. FIG. 13B (scaffold alone) shows some initial osteophyte formation at the junction between the bone and the fiber scaffold that was placed within the defect. This suggests that the fiber scaffold institutes at least some bone repair, as evidenced by the data of FIG. 13A. In FIG. 13C, the histology suggests that the addition of the lyophilized/sterilized microvascular tissue resulted in true bone formation at the margins of the scaffold. Thus, within the same time period, microvascular tissue facilitated the formation of bone, rather than the demineralized precursor to bone. This suggests that the use of microvascular tissue in conjunction with a scaffold can accelerate the healing process.

With respect to cartilage repair, 4 mm×7 mm critical-sized defects were punched into the cartilage on the medial trochlecar groove of mature goats. The defects were approximately 1 mm deep, which is slightly deeper than the cartilage. Tissue scaffolds (BIOFIBER, Tornier) either alone or supplemented with lyophilized/sterilized microvascular tissue (~$10^6$ cells) were fitted into the defects and held in place with a 7-0 nylon suture at each corner. After 3 months the defects were examined histologically. This data is shown in FIGS. 14A-14H. FIGS. 14A-14D show data from the scaffold alone, while FIGS. 14E-14H show data from the microvascular tissue supplemented scaffold. FIG. 14A shows a macroscopic view of the scaffold on the previously damaged cartilage, while FIG. 14E shows the same view for the scaffold supplemented with microvascular tissue. Both treatment groups showed evidence of repair. FIGS. 14B and 14F show hematoxylin and eosin staining of the cartilage. The use of the scaffold including microvascular tissue showed improved fill in margins as compared to the use of scaffold alone. FIGS. 14C and 14G show safranin O staining, and reveal a greater degree of proteoglycans and retention in the defects treated with microvascular tissue. FIGS. 14D and 14H show toluidine blue staining of the defects, and reveal that the newly generated cartilage matrix stains more like mature cartilage when microvascular tissue was used to treat the defect. Together these data, as with the bone experiments above, confirmed that microvascular tissue facilitates the repair of cartilage.

Figure 15A:
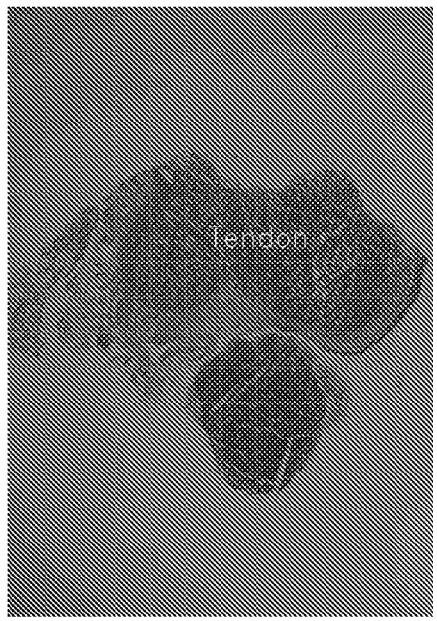
Figure 15B:
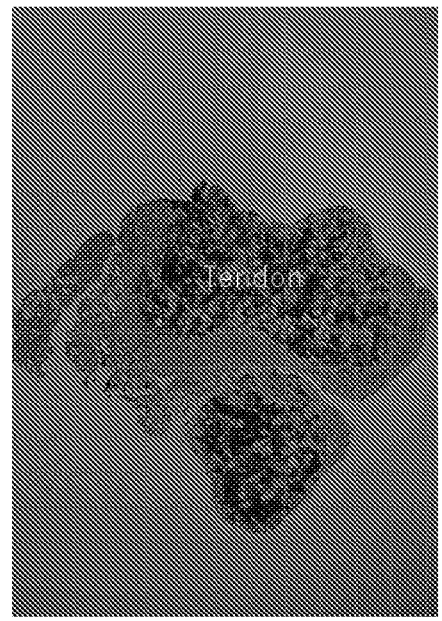
Figure 15C:
Figure 15D:
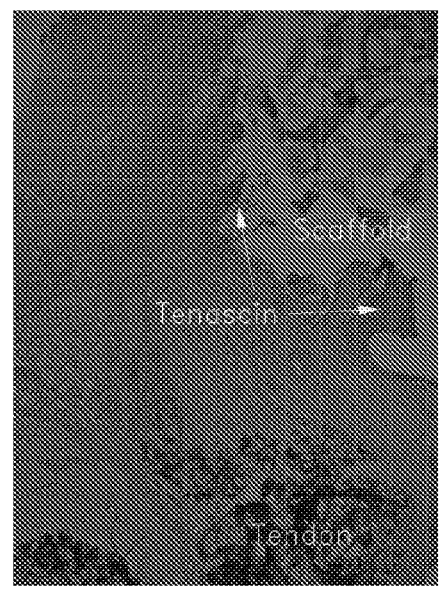

Experiments were also performed to evaluate the ability of microvascular tissue to repair tendon. Rat achilles tendons were exposed and abraded with mouse-tooth forceps. Controls were operated on in the same manner. One group of rats was treated with scaffold alone and another with scaffold supplemented with lyophilized/sterilized microvascular tissue. Rats were sacrificed for qPCR, histology and immunohistochemistry after 7 days. The Scaffold group received a 4 mm×7 mm BIOFIBER-CM Scaffold on the anterior surface of the Achilles. The scaffold was loaded with $10^6$ microvascular cells in the microvascular tissue and treatment group. Control data is shown in FIGS. 15A (Masson's trichrome stain) and 15B (immunohistochemistry for tenascin). Data for the scaffold group is shown in FIGS. 15C and 15D. Masson's trichrome staining (FIG. 15C) revealed small pockets of dense collagen in and around the scaffold, indicative of initial tendon repair. Similarly, immunohistochemistry staining for tenascin (FIG. 15D) revealed increases in expression at the margin between the tendon and implanted scaffold, again suggestive of initial repair of the defect.

Data for the microvascular tissue group is shown in FIGS. 15E and 15F. Masson's trichrome staining (15E) revealed substantial formation of dense collagen in and around the scaffold, indicative of considerable repair of the defect. Similarly, immunohistochemistry staining for tenascin revealed extensive expression between the tendon and implanted scaffold. These data are also indicative of significant repair of the defect.

Taken together, the data presented in these experiments establish that microvascular tissue is capable not only of angiogenesis (which plays an important role in establishing and maintaining blood supply to a target tissue), but are also capable of enhancing the repair of bone, cartilage, and tendon. In several embodiments, the enhanced angiogenesis, at least in part, plays a role in the ability of microvascular tissue to result in the generation and maintenance of new tissue.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering microvascular tissue" include "instructing the administration of microvascular tissue." The ranges disclosed herein also encompass any and all overlap, subranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm."

What is claimed is:

1. A method of preparing a composition comprising processed microvascular tissue, wherein the composition has angiogenic or anti-inflammatory activity, the method comprising:
    (a) dissociating a microvascular tissue sample obtained from a donor mammal to produce a composition comprising dissociated microvascular tissue;
    (b) removing one or more tissue components from the composition produced according to (a);
    (c) optionally drying, lyophilizing, or cryopreserving the composition following (b) or (d); and (d) sterilizing the composition following (b) or (c) and/or inactivating virus present in the composition following (b) or (c);

wherein the composition resulting from (c) or (d) retains measurable angiogenic or anti-inflammatory activity;

wherein:
(i) the cells or tissue are not cultured;
(ii) the method further comprises filtering the composition;
(iii) the dissociation of (a) comprises contacting the tissue sample with one or more proteases; and
(iv) the dissociation of (a) or the removing of (b) comprises ultrasonic agitation, centrifugation, filtration, or use of a density gradient; and further wherein
(v) the one or more proteases does not comprise collagenase;
(vi) the one or more proteases comprises or consists of: collagenase type 1 and either dispase or thermolysin; or MMP 2, MMP 14 and either dispase or thermolysin; or
(vii) the microvascular tissue is adipose-derived tissue, and the ultrasonic agitation, centrifugation, filtration or use of a density gradient removes adipocytes from the composition produced according to (a).

* * * * *